United States Patent [19]
de la Huerga et al.

[11] Patent Number: 5,903,889
[45] Date of Patent: May 11, 1999

[54] SYSTEM AND METHOD FOR TRANSLATING, COLLECTING AND ARCHIVING PATIENT RECORDS

[75] Inventors: Carlos de la Huerga, River Hills, Wis.; William E. Craig, San Antonio, Tex.

[73] Assignee: Telaric, Inc., San Antonio, Tex.

[21] Appl. No.: 08/871,818

[22] Filed: Jun. 9, 1997

[51] Int. Cl.[6] .................................................. G06F 17/30
[52] U.S. Cl. ................................. 707/3; 707/10; 707/104
[58] Field of Search ............................ 707/10, 104, 102, 707/3

[56] References Cited

U.S. PATENT DOCUMENTS

| | | | |
|---|---|---|---|
| 3,872,448 | 3/1975 | Mitchell | 340/172.5 |
| 4,817,050 | 3/1989 | Komatsu et al. | |
| 4,893,270 | 1/1990 | Beck et al. | 707/10 |
| 4,958,283 | 9/1990 | Tawara et al. | 364/413.13 |
| 5,065,315 | 11/1991 | Garcia | |
| 5,146,439 | 9/1992 | Jachmann et al. | 369/25 |
| 5,218,697 | 6/1993 | Chung | |
| 5,253,362 | 10/1993 | Nolan et al. | 707/102 |
| 5,361,202 | 11/1994 | Doue | |
| 5,377,323 | 12/1994 | Vasudevan | 395/200 |
| 5,408,655 | 4/1995 | Oren et al. | |
| 5,459,860 | 10/1995 | Burnett et al. | 707/104 |
| 5,506,984 | 4/1996 | Miller | 707/104 |
| 5,530,852 | 6/1996 | Meske, Jr. et al. | 707/10 |
| 5,646,416 | 7/1997 | Van De Velde | 250/584 |

*Primary Examiner*—Thomas G. Black
*Assistant Examiner*—Frantz Coby
*Attorney, Agent, or Firm*—Akin, Gump, Strauss, Hauer & Feld, L.L.P.

[57] ABSTRACT

A system for retrieving, modifying, and collecting data records having a plurality of formats and distributed on a plurality of databases on a computer network. The system includes means for detecting various types, relationships, and classifications of data records and modifying them accordingly to support interactive, hypertext-linked display of, and organized access to, the data records. The system further includes means to store a related set of data records on a mass storage device such as a CD-ROM to provide non-network access to the data records. Adapted for use in a hospital environment, the invention facilitates access by care providers, administrators, and insurance company agents to a patient's cumulative, and possibly extensive, record.

47 Claims, 24 Drawing Sheets

| Database Table | | | |
|---|---|---|---|
| Database 1 Register | Address(es) | File Format Instruction Table 1 | |
| ⋮ | | | |
| Database N Register | Address(es) | File Format Instruction Table N | |

Figure 3A

| File Format Instruction Table | | | |
|---|---|---|---|
| Data Type 1 | Hypertext Cipher | URL Cipher | Special Instructions To Retrieve Data |
| ⋮ | | | |
| Data Type M | Hypertext Cipher | URL Cipher | Special Instructions To Retrieve Data |

Figure 3B

| Workstation Data Table | | |
|---|---|---|
| Workstation 1 | Address | File Access Commands |
| ⋮ | | |
| Workstation N | Address | File Access Commands |

| Workstation File Formatting Instruction Table | | |
|---|---|---|
| Report 1 Name | File Name & Data Formatting Instructions | Workstation URL Cipher |
| ⋮ | | |
| Report M Name | File Name & Data Formatting Instructions | Workstation URL Cipher |

```
<html>
<body>

<font size=6>Charles F. Smith<br>
font size=4> Medical records from 15-AUG-1998 to 23-AUG-1998<br>
Community Hospital, Springfield<br><br>

<a href="demographics.html">Demographics</a><br>
<a href="admission_report.html">Admission Report</a><br>
<a href="/cardiology.html">Cardiology</a><br>
<a href="/laboratory.html">Laboratory</a><br>
<a href="/vital_signs.html">Vital Signs</a><br>
   •
   •
   •
<a href="discharge_report.html">Discharge Report</a><br>

</body>
</html>
```

Figure 6A

Charles F. Smith
Medical records from 15-AUG-1998 to 23-AUG-1998,
Community Hospital, Springfield

Demographics
Admission Report
Cardiology
Vital Signs
   •
   •
   •
Discharge Report

Figure 6B

412
```
<html>
<body>
DISCHARGE SUMMARY for Charles F. Smith<br><br>

Date of Admission: 15-AUG-98<br>
Date of Discharge: 17-AUG-98<br><br>

HISTORY OF PRESENT ILLNESS:<br>
Patient #1 is a 47-year-old male admitted for further evaluation of recent exertional
angina and abnormal exercise test.<br><br>
```

416
```
HOSPITAL COURSE:<br>
The patient was admitted to the Telemetry unit and underwent <a
href="charles_f_smith/cardiology/cath/1998-08-15/10:25/report.html">cardiac
catheterization on August 15, 1998</a>. Catheterization demonstrated normal
ventricular function without evidence for prior infarction. The coronary arteriogram
showed moderate stenosis throughout the mid and distal portions of the left anterior
descending artery and diagonal branch, as well as • • ••
```

DISCHARGE SUMMARY for Charles F. Smith

Date of Admission: 15-AUG-98
Date of Discharge: 17-AUG-98

HISTORY OF PRESENT ILLNESS:
Patient #1 is a 47-year-old male admitted for further evaluation of recent
exertional angina and abnormal exercise test.

HOSPITAL COURSE:<br>
The patient was admitted to the Telemetry unit and underwent catheterization on August 15, 1998. Catheterization demonstrated normal ventricular function without evidence for prior infarction. The coronary arteriogram showed moderate stenosis throughout the mid and distal portions of the left anterior descending artery and diagonal branch, as well as • • ••

Figure 7B

418
```
<html>
<body>

<font size=6>Charles F. Smith<br>
font size=4>Cardiology records from 15-AUG-1998 to 23-AUG-1998<br>
Community Hospital, Springfield<br><br>

<a href="/ecg/list.html">Ecg Reports</a><br>
<a href="cath/1998-08-15/10:25/report.html">Catheterization Procedure</a><br>
<a href="/stress/list.html">Stress Tests</a><br>
<a href="holter/1998-08-19/11:04/report.html">Holter</a><br>
        •
        •
        •
<a href=""nuclear/1998-08-20/14:54/report.html">Nuclear Scan</a><br>

</body>
</html>
```
420
422

Figure 8A 418
118
420

Charles F. Smith
Cardiology records from 15-AUG-1998 to 23-AUG-1998,
Community Hospital, Springfield

Ecg Reports
Catheterization Procedure
Stress Tests
Holter
    •
    •
    •
Nuclear Scan

```
424 ┐  <html>
        <body>

<font size=6>Charles F. Smith<br>
        font size=4>ECG records from 15-AUG-1998 to 23-AUG-1998<br>
        Community Hospital, Springfield<br><br>

<a href="ecg/1998-08-15/09:15/report.html">15-AUG-1998
        09:15</a><br>
        <a href="ecg/1998-08-15/16:40/report.html">15-AUG-1998
426     14:40</a><br>
        <a href="ecg/1998-08-17/11:03/report.html">17-AUG-1998
        11:03</a><br>
                                              •
                                              •
        <a href="ecg/1998-08-19/10:25/report.html">19-AUG-1998
        09:15</a><br>
```

Figure 9A

118 — Charles F. Smith
Ecg records from 15-AUG-1998 to 23-AUG-1998,
Community Hospital, Springfield

15-AUG-1998 09:15
15-AUG-1998 14:40
17-AUG-1998 11:03
19-AUG-1998 09:15
426
•
•
•

23-AUG-1998 08:14

Figure 9B

SYSTEM AND METHOD FOR TRANSLATING, COLLECTING AND ARCHIVING PATIENT RECORDS

FIELD OF THE INVENTION

The present invention relates to the collection, storage, and retrieval of data on computer systems. More particularly, the present invention relates to a computer system for retrieving, modifying, and storing a plurality of topically, textually, or audio-visually related data records of a plurality of formats on a plurality of databases in conformance with a hypertext-linked, predefined topical organization.

BACKGROUND OF THE INVENTION

When a patient is in a hospital, either as an inpatient or an outpatient, a variety of information concerning the patient may be collected and recorded. This may be in the form of observations, measurements, Dab results, vital sign indicators, procedure reports and associated graphics. Over a long period of treatment, hundreds of pages of information may accumulate in the patient's record.

While the patient is in the hospital, it is typical that many different care givers, administrators, or insurance company employees will desire to view a part of the patient's cumulative record. The conventional paper chart is not always useful, as there is only one copy of it, and some laboratory tests may not be entered into the chart on a timely basis. To solve this problem, hospitals have used a variety of database systems such as hospital information systems (HIS) and clinical information systems (CIS) to store and present patient information on computer displays. However, there is still a substantial amount of data that does not get placed into these systems. A variety of factors may inhibit an automated process of comprehensive retrieval of a patient's data, such as incompatible communication protocols and formatting schemes between computer systems, non-digitized data records including pictures and standardized forms, and the lack of adequate computer interfacing support for low-cost medical instruments or devices. It is also typical that word processing documents, rather than being automatically collected by a database system, are simply printed in the form of a paper copy to be inserted into the conventional chart.

While various standardization committees have been established, e.g., HL-7, DOCOM, and IEEE, to develop common addressing schemes for hospital data, to date none have defined a consistent format to use for storing and retrieving data. For the sake of simplicity or due to limited resources, many manufacturers that use one or more of these standards choose to use only a portion of them; consequently their systems remain only partially compatible.

Furthermore, even many hospitals with database systems lack a centralized retrieval system because related hospital reports are often stored on separate databases. For example, a patient's radiology catheterization report and hemodynamic catheterization reports may be created and stored in separate databases, though as far as the physician who performed the catheterization procedure is concerned, these two reports are really just one procedure and should be associated with each other. For further example, a physician reviewing an admission report may find that it references laboratory tests or observations made contemporaneous with or previous to the patient arriving at the hospital. Should the physician decide to review these other records, she will have to perform additional searches to locate them. In some cases, this often cumbersome and time-consuming process results in care givers refraining from making complete use of the available patient information.

In many hospitals when a patient is discharged, a paper copy of these records is made and sent to the admitting physician for his own record keeping purposes. The collection, copying, and storage of all of these records is a very time-consuming and labor-intensive activity. Further, the generally high risk of human error may manifest itself in the failure to return records to the correct patient's file or incorrect storage of a patient's entire file, effectively forfeiting the misplaced information. The physician is simultaneously confronted with the responsibility of filing and storing the paper copy in his own office.

Some hospitals have purchased laboratory or information systems capable of long term storage of various records. While this may assist the hospital in retrieving past records, it may not help the admitting physician in referring to them, for he may not have access to the data directly or may not have the specific software required to retrieve the data. So with such advanced systems the physician is still provided with a paper copy for his records.

Furthermore, many existing laboratory and information systems record information in a variety of inconsistent formats. Some of these formats are proprietary to the manufacturer of the specific system. Each system may use a separate database scheme to gain access to the data. Substantial efforts to get these systems to communicate with each other have not yielded satisfactory results. For example, many large medical information systems use complicated data exchange protocols; but these protocols are unwieldy for simple, often portable instruments which lack the hardware and software capacity to conform to such protocols.

Some reports may be created using a word processor. These may originate in a department of the hospital or in a physician's office. These reports, which may be kept in a conventional file cabinet, are not always included with the rest of the patient's reports.

What is needed is an effective alternative to creating paper records that must be copied and meticulously tracked, an alternative that would permit physicians to access the data economically and easily in their own offices. Such a system would permit a system user to enter a keyword to retrieve a specific data record of a patient, retrieve the requested record from whichever database it is stored to, reformat the data record with hypertext links to related patient records, and return the requested record to the system user for display on a browser. The system would preferably use the well-known Hypertext Markup Language (HTML) so that it could utilize inexpensive, standard software packages. The system would also be operable to format data records stored on the various databases of the computer network systematically, periodically, or automatically upon the creation of new, or the modification of existing, data records. The system would be operable to collect all data records pertaining to a specific patient, doctor, or other subject, modify them to support display through a Java applet, internet browser, or other universal display standard, generate additional patient files to organize the data records in a hypertext directory structure, and store the data records and files on a mass-media storage device such as a CD-ROM.

SUMMARY OF THE INVENTION

It is an object of this invention to provide a means of processing and converting existing data records formatted, structured, and accessed according to a multitude of disparate standards to common standards by which they may be accessed, controlled, and/or displayed through a single interactive display program. It is another object of this invention to provide conventions for exploring data records for references to contextually related data records and modifying, generating, embedding, and appending links and data-retrieving codes in and to said related data records, whereby to organize said related data records in a hypertext tree structure. A further object of this invention is to store a group of related data records organized in a hypertext tree structure to a mass storage device, such as a hard disk or CD-ROM, through which the data records may be retrieved, displayed, and controlled through a single interactive display program. In order to minimize costs and maximize end-user accessibility, the standards and conventions used by the present invention for modifying data records and addressing schemes facilitate display through a widely-familiar and low-cost display program such as an Internet browser.

The invention may be adapted for use in a wide variety of applications, and is suitable for any environment in which numerous data records having one or multiple forms and/or formats are to be collected, stored, archived, retrieved, or translated. By way of illustration and not by way of limitation, the invention is presented in the context of a hospital environment, in which typically there are numerous computer systems in use by various health care professionals in one or several hospitals, and each professional often desires to have access to the patient records created by other professionals in that or other hospitals.

A typical setting for the present invention provides multiple databases and workstations linked via a network wherein the databases store data records in a variety of formats and the workstations utilize user interfaces to input, retrieve, and manipulate data records. The present invention utilizes specification tables identifying each of the information processors or databases used by the hospital, the types of data records stored by the databases, and instructions and algorithms for accessing, modifying, and processing data records and their addresses, depending on the data type. Similar specification tables are also kept to identify each workstation where word processor, spreadsheet, or other records, including those downloaded from portable medical devices, may be held.

When a system user at a workstation linked to the hospital computer network equipped with the present invention submits a request for a particular patient record, the invention parses the data request for an address root and other pertinent information about the data record to be retrieved, which may include the time and date the data record was created or last modified and a patient ID. Using this information incorporated in the data request and in the specification tables, the invention modifies the existing data request into a URL or other addressing convention, as necessary, to retrieve the data record from the appropriate database.

After retrieving the data record, the invention may modify it to make it compatible with a standard supported by the common interactive display browser used by the system. For example, the invention may convert a text document to an HTML document or convert graphics, video, or audio records to browser or Java-enabled formats. Further, depending on the formatting specifications for a particular data type, the invention may identify key words, links, and programming codes embedded in the data record, modifying them and inserting additional hypertext links and programming codes as necessary. For example, it may be desirable that a hypertext link referencing the patient's demographics and insurance information be inserted into each record reporting on the patient's condition, status, or profile for quick and easy referral. As another example, it may be desirable to place a hypertext link in a radiology catheterization report that references the hemodynamic catheterization report and vice versa so that each refers to the other.

In this manner a hospital may use internet or Intranet compatible databases with databases that are not compatible, and may choose to use URL addresses of its own choice independent of what the individual vendors have chosen. The administrator may also preprogram the data translation and collection system to link reports together as appropriate, so that care givers may more quickly and directly refer to relevant or related information. The translation process described here may be used on a dedicated system for this purpose or may be distributed among several processors including those of the database systems.

Another aspect of the present invention includes means for receiving, processing, and storing hospital records systematically, periodically, or automatically as they are created or modified. In this mode of operation data records may be preformatted according to the hospital's specifications, allowing for quicker record retrieval during subsequent data requests. The translation operation may be allocated to a dedicated system for this purpose or may be distributed among several processors, including those of the database systems.

A further aspect of the present invention includes means for periodically retrieving and filing the contents of a designated area of each workstation's disk. For example, word processing documents generated at a workstation may be stored in a designated area, such as a special "collection" drive or folder, to which the hospital computer network has access. The invention would retrieve the data records stored in the collection folder, and identify, interpret, and modify them before storing them in an appropriate database.

Yet another aspect of the present invention includes means for retrieving, processing, and storing all of a patient's data records that are available on the hospital's computer network onto a mass media storage device, such as a CD-ROM. For example, this process may be initiated by submitting a collection request identifying the patient's OD number or other identifier uniquely identifying the patient. The invention submits requests, passwords, macros, and programming codes, as appropriate, to each of the databases and workstations that include portions of the patient's cumulative record. Each record retrieved is processed and modified as above—as if the particular record had been requested by a system user. The invention not only collects applicable data records, but also multimedia clips, applets, browser extensions, "plug-ins," and other application modules addressed by programming codes embedded in the patient's data records. Substitute files explaining the absence of a linked record or module are created for data records or modules regarded as inappropriate for storage and distribution on an unsecured or uncontrolled medium. The invention would also create a "master file for the patient analogous to a "home page" for a website or the root directory of a tree structure, containing links to other patient-related files and data records. The master file may have hypertext links to patient records and to additional (secondary) control files, which in turn have hyperlinks to more patient data. After completing these collection routines, the invention would transfer the collection of data records, applets, browser extensions, and other data and programming modules to a mass-storage device. In this manner a patient's cumulative patient record could be stored on a single CD-ROM or other high-density storage device, cheaply distributed to other hospitals or health care professionals serving the patient, and be conveniently accessed by those hospitals and health care professionals.

BRIEF DESCRIPTION OF THE DRAWINGS

The present invention is more easily understood with reference to the drawings, in which:

FIGS. 3A and 3B are tables showing the contents of the "Database Table" and "File Format Instruction Table" maintained and used by the data translation and collection system to access, translate, reformat, and store data records kept on databases on the medical computer network.

FIGS. 4A and 4B are tables showing the contents of "List of Workstations" and "Report List" maintained and used by the data translation and collection system to access, translate, reformat, and store data records kept on workstations on the medical computer network.

FIG. 6A is a graphical representation of a master file in HTML format through which all of a single patient's medical records created at a hospital equipped with the present invention may be viewed.

FIG. 6B is a graphical representation of the master file of FIG. 6A as viewed by a system user with a network browser.

FIG. 7A is a graphical representation of a secondary control file in HTML format providing a hypertext-link embedded discharge report.

FIG. 7B is a graphical representation of the secondary control file of FIG. 7A as viewed by a system user with a network browser.

FIG. 8A is a graphical representation of another secondary control file in HTML format providing a structured list of hypertext links to a plurality of cardiology reports.

FIG. 8B is a graphical representation of the secondary control file of FIG. 8A as viewed by a system user with a network browser.

FIG. 9A is a graphical representation of a tertiary control file in HTML format providing a list of electrocardiogram reports.

FIG. 9B is a graphical representation of the tertiary control file of FIG. 9A as viewed by a system user with a network browser.

DETAILED DESCRIPTION OF THE PREFERRED EMBODIMENTS

Figure 1:
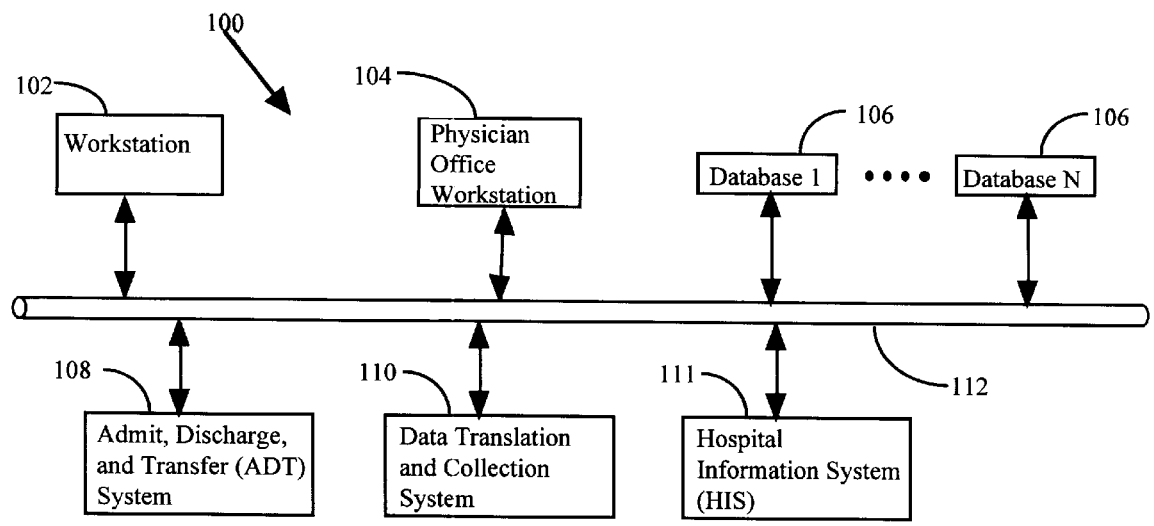
FIG. 1 is a block diagram of a medical computer network according to the present invention, including a plurality of databases for data record storage and a data translation and collection system.

Referring now to FIG. 1, the invention is illustrated as a medical computer network 100, including a plurality of hospital based workstations 102 (which may be personal computers), a plurality of physician office workstations 104 which may also be personal computers, a plurality of databases 106 which may be provided by a multitude of vendors with separate data structures and data elements. The computer network 100 may also comprise an Admit, Discharge, and Transfer (ADT) system 108, a data translation and collection system 110, and a Hospital Information Systems (HIS) 111. The data translation and collection system 110 is not necessarily a separate physical element of the medical computer network 100, but is represented that way in the preferred embodiment for purposes of illustration only. It may be alternately recognized as a program application or even an aspect of a network operating system, the operations of which may be distributed over and performed by many different processors, workstations, and databases on the medical computer network 100. Databases 106, computer systems 108, 110, 111, workstations 102, and physician office workstations 104 may communicate with each other via a communication network 112, which may be a combination of local and wide area networks, using Ethernet, serial line, wireless, or other communication standards. Communication network 112 may also be arranged in such a manner to be part of the Internet or as an individual Intranet. Workstation 102, 104 includes a "collection" folder 105 and a user interface 103 which may include a network browser or similar display, entry, and retrieval program. User interface 103 may be any means for permitting users to create data records and/or retrieve data records from the medical computer network 100 capable of supporting a network browser, such as the well known keyboard and video terminal combination.

Figure 2:
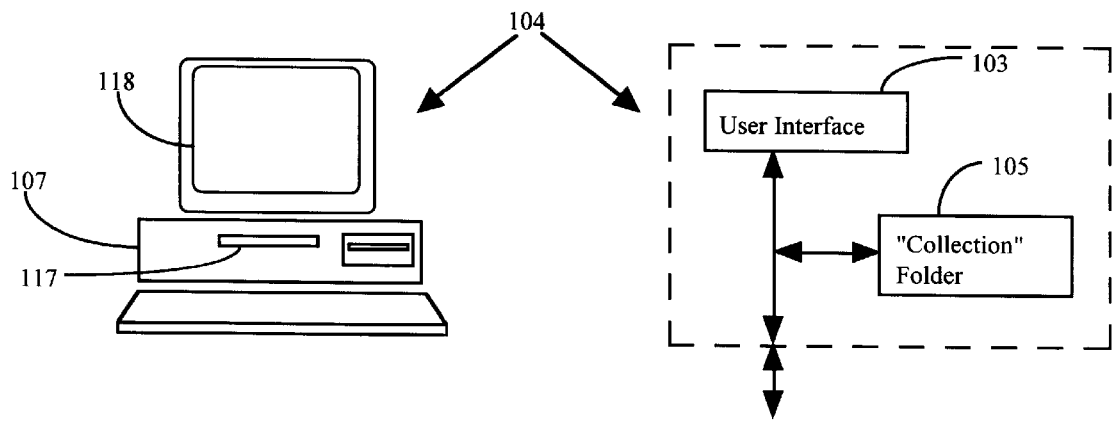
FIG. 2 is a graphical illustration of a physician office workstation.

FIG. 2 shows a typical physician office workstation 104 comprising a personal computer 107 which may include a display 118, and a CD-ROM drive 117 or other means of mass storage which may be removable.

The data translation and collection system 110 maintains a file referred to as Database Table 130, whose contents are partially seen in FIG. 3A. For each database 106 included on the medical computer network 100, an entry is made in the Database Register 131 of the Database Table 130. Corresponding to each entry in the Database Register 131 is an address or addresses fiend 132 used to access the database on communication network 112 and a separate File Format instruction Table 134.

A partial list of the contents of File Format Instruction Table 134 is seen in FIG. 3B, which includes records of each data type 136 stored by the database 106. Corresponding to each data type 136 in File Format Instruction Table 134 is a set of special instructions or program codes 142 used to translate a request for such date to a format appropriate to the data type and database from which the requested information may be retrieved. Also corresponding to each data type 136 is a hypertext cipher 138 providing special instructions or codes used to add data references (such as hypertext links) and to format the data, which instructions or codes may include decompression algorithms. Further corresponding to each data type 136 is a URL cipher 140 used to generate an address to store the designated type of data.

Figure 10:
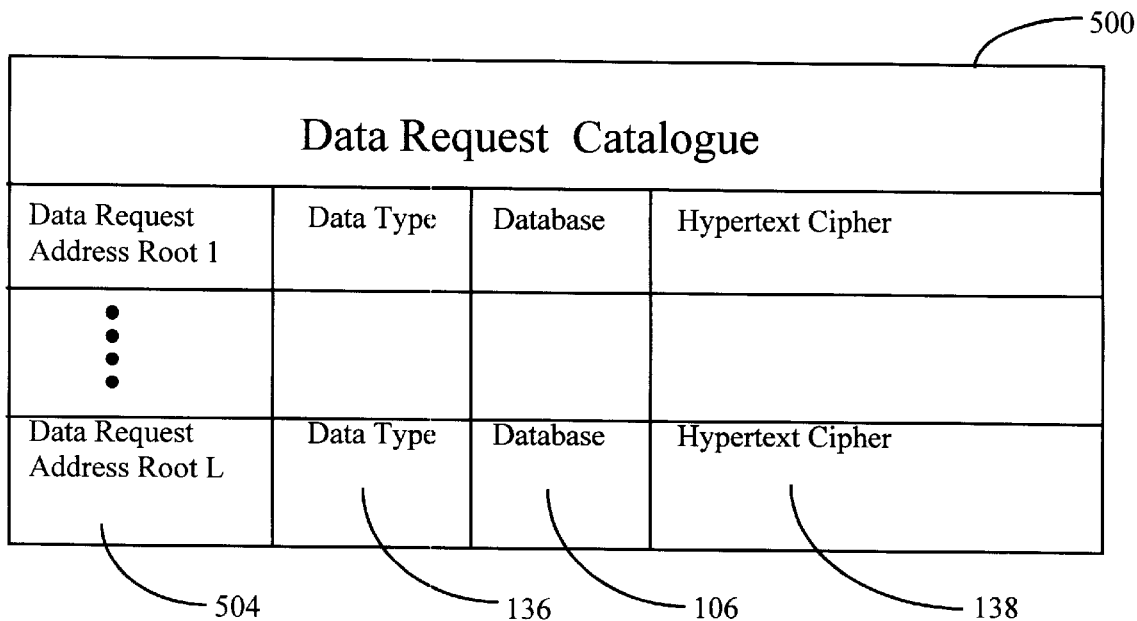
FIG. 10 is a table showing the contents of the "Data Request Catalogue" maintained and used by the data translation and collection system to discriminate the data type and database location of a requested data record from the alphanumeric string requesting the data.

The data translation and collection system 110 may also retain a file referred to as Data Request Catalogue 500, whose contents are partially seen in FIG. 10. The Data Request Catalogue 500 includes an array of Data Request Address Roots 504, to each element of which corresponds fields identifying the data type 138, the database 106 in which the data type is located, and hypertext cipher 138 (which is kept also in the File Format Instruction Tables 134 (FIG. 3B) of the Database Table 130 (FIG. 3A)). This file may be accessed when a request for data is received by the data translation and collection system 110 to recognize the matching data request address root 504 which identifies the data type 136 and the database 106 on which it is kept.

A. Responding to Data Requests and Providing Translation

Figure 12A:
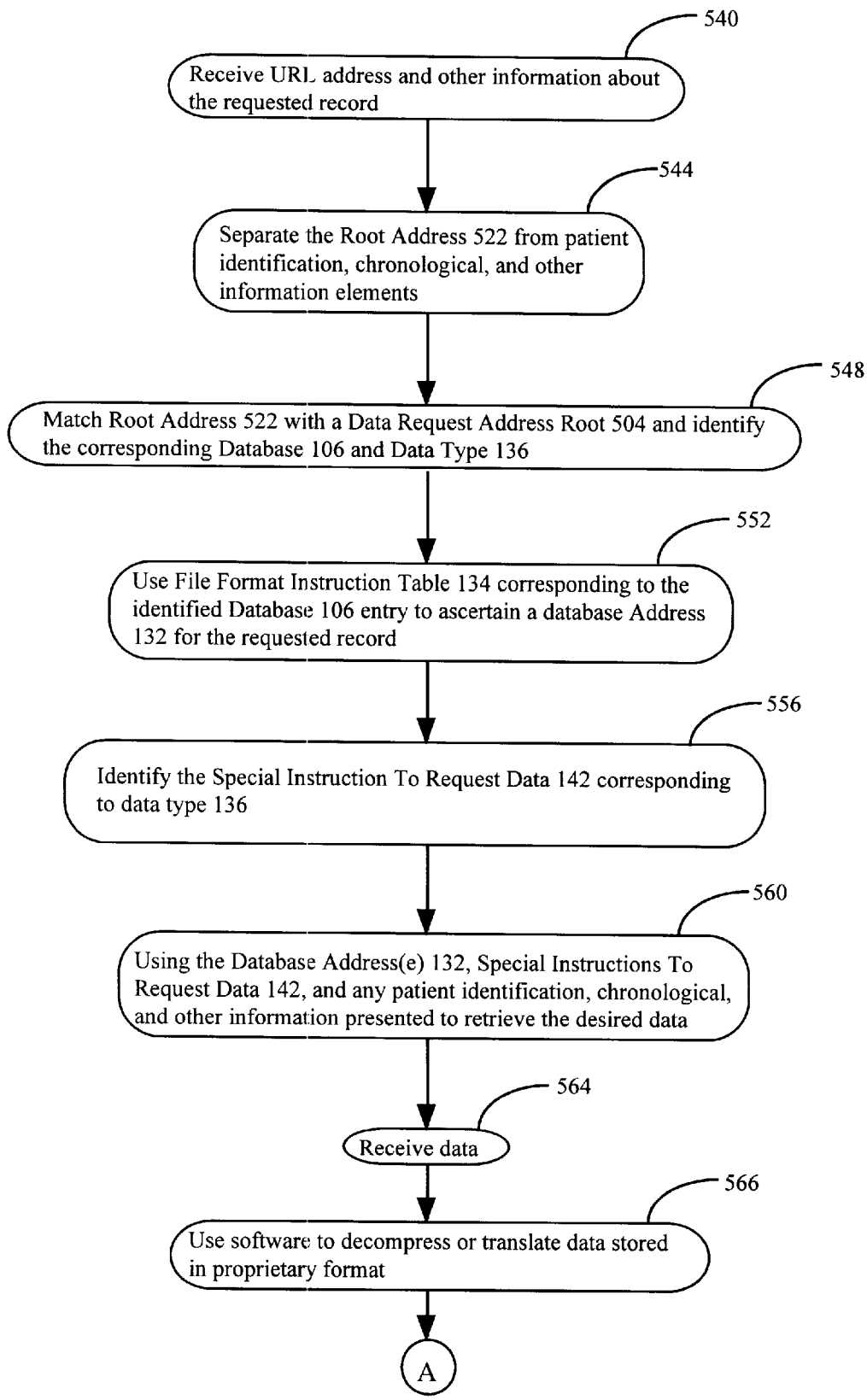
FIGS. 12A–12C are a functional flow chart showing the steps used to receive a request for a data record, translate the request, retrieve the data record, and reformat the data record prior to sending it to its requested destination.
Figure 12B:
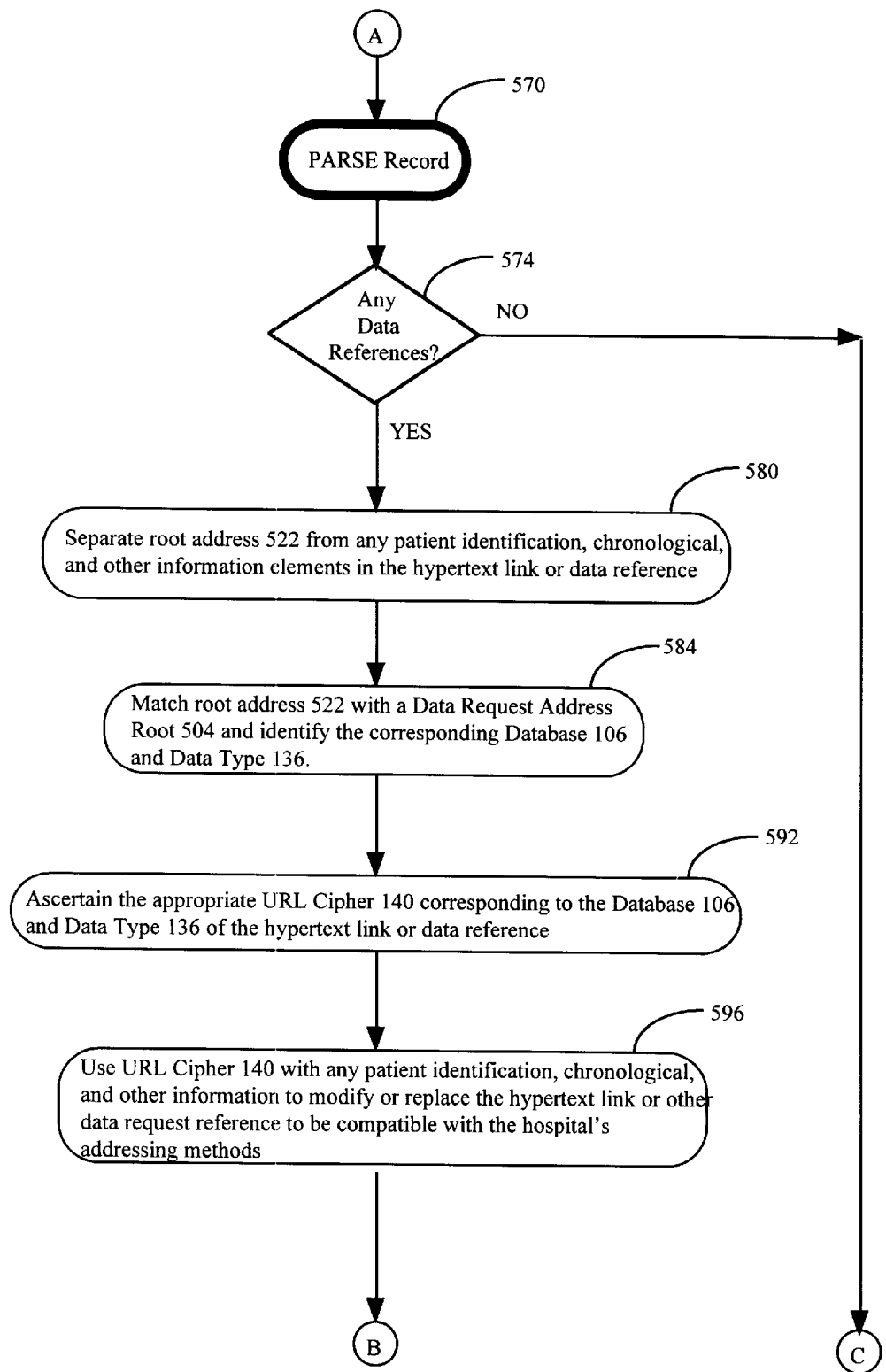
Figure 12C:
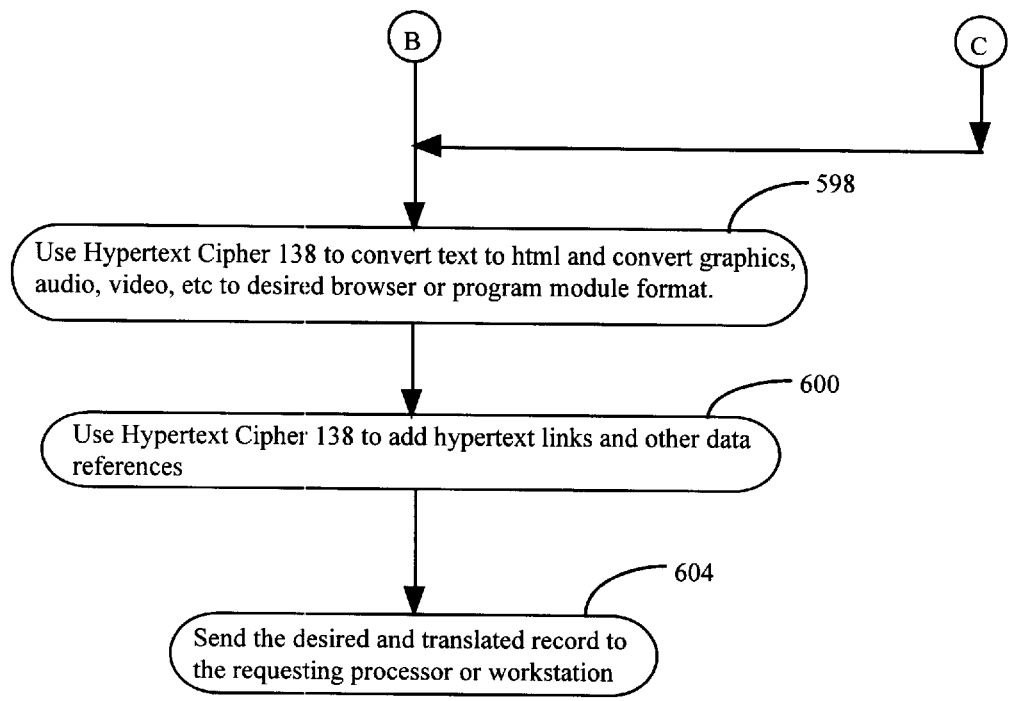

FIGS. 12A–12C describe the operation of the data translation and collection system 110 (FIG. 1) in responding to requests to retrieve data, translating those requests to conform to the format required by the applicable database, retrieving the data, reformatting the data, and delivering the data to the appropriate destination.

Figure 11:
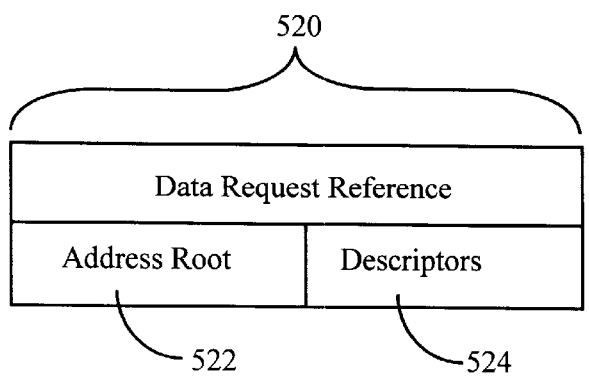
FIG. 11 is a graphical representation of a data request containing an address root and descriptor.

Commencing with FIG. 12A, in step 540 the data translation and collection system 110 receives a data record reference 520 (FIG. 11) in the form of a data request containing an address root 522 and descriptors 524 about the requested record. In some instances, a data request will originate from a system user accessing a hypertext link on a document displayed by the system's interactive display browser. In other instances, the data request will originate from a database or workstation application program. There may be several non-uniform but mutually distinguishable data request formats among the several hospital databases 106 (FIG. 1) on the medical computer network 100 (FIG. 1). Alternately, data requests may be uniformly and compatibly formatted for all records stored by various hospital databases 106 (FIG. 1). For example, the data requests may be in the form of a URL with optional data fields sent with it to assist in identifying the record to be retrieved.

In step 544, the address root 522 (FIG. 11) of the data record reference 520 may be determined by removing the descriptors 524—any patient identification, chronological details, or other non-addressing information—from the received data request. The descriptors 524 are temporarily stored for use in step 560.

In step 548, a search is performed to locate a match for the address root 522 (FIG. 11) of the data record reference 520 among the data request address roots 504 (FIG. 10) listed in the data request catalogue 500 (FIG. 10). By finding a matching data request root address 504, the invention immediately identifies the data type 136 (FIG. 10), the database 106 used to store this data, and the hypertext cipher 138 providing special instructions used to format and add data references to the data.

In step 552 the database 106 identified in step 548 is in turn referenced in Database Table 130 (FIG. 3A) to its corresponding File Format Instruction Table 134 (FIG. 3A) to determine the address(es) 132 (FIG. 3A) of the database 106 storing the data.

In step 556 the data type 136 identified in step 548 is cross-referenced with the File Format Instruction Table 134 (FIG. 3A) identified in step 552 to locate the special instructions to request data 142 (FIG. 3B) used to translate the request to a format appropriate to the data type and database from which the requested information may be retrieved. These instructions may, for example, include passwords or macros needed to retrieve the data.

In step 560 a code is constructed using the database address(es) 132 identified in step 552, the special instructions to request data 142 identified in step 556, and the descriptors 524—the patient identification, chronological details, or other non-addressing information—stored in step 540. The code is submitted to the appropriate database to produce the requested data record.

After the database has produced the requested data record, the record may in step 564 be received by the data translation and collection system 110 for additional processing.

The steps by which the data translation and collection system 110 processes the selected data record are shown in FIGS. 12B and 12C. In step 566, the system uses the hypertext cipher 138 to determine whether or not the data is stored in a proprietary format. If it is, the applicable proprietary software is used to decompress or translate the data. This may be done on the manufacturer's database 106, another computer processing system, or by the data translation and collection system 110 a itself.

In step 570, the record is parsed, discussed infra, to locate date references: hyptertext links, multi-media requests, and key words or phrases. If none are found, the process advances to step 598, discussed infra.

If there are data references, they may in steps 580 through 596 be reformatted so that the URL addresses are compatible with addressing protocols used by the hospital. In step 580, the address root 522 (FIG. 11) of the hypertext link or other data record reference 520 may be determined by removing the descriptors 524—any patient identification, chronological details, or other non-addressing information—from the received data request. The descriptors 524 are temporarily stored for use in step 596. In step 584, a match for address root 522 is sought among the data request address roots 504 (FIG. 10) listed in Data Request Catalogue 500, which locates the Database 106 and Data Type 136 corresponding to the matching Data Request Address Root 504. In step 592, the identified Database NO and Data Type 136 are referenced in Database Table 130 (FIG. 3A) and the corresponding File Format Instruction Table 134 (FIG. 3B) to acquire the appropriate URL cipher 140 (FIG. 3B). In step 596, the URL cipher 140 processes the descriptors 524—the patient identification, chronological detail, and other information—extracted in step 580 to modify or replace the hypertext link or other data reference found in the selected record. Steps 580 through 596 may be performed for each hypertext link and reference to other data records found in the selected record.

For some types of data records, the URL cipher 140 will generate addresses compatible with database formatting standards such as SQL or Oracle.

In step 598 the data translation and collection system 110, using the Hypertext Cipher 138, converts any text portion of the selected data record into a browser compatible format, such as HTML format, and any graphics, audio, video, or other non-text information into a browser, plug-in, or Java compatible format.

In step 600, the data translation and collection system 110 inserts hypertext links or other references to the selected record in accordance with the hypertext cipher 138 identified in step 548. If directed by the hypertext cipher 138, the record may also be interpreted and modified or reformatted.

In step 604, the data translation and collection system 110, having retrieved and translated the requested record, forwards the record to the destination selected by the requesting workstation or processor.

B. Receiving Patient Records for Translation and Address Formatting

Figure 13A:
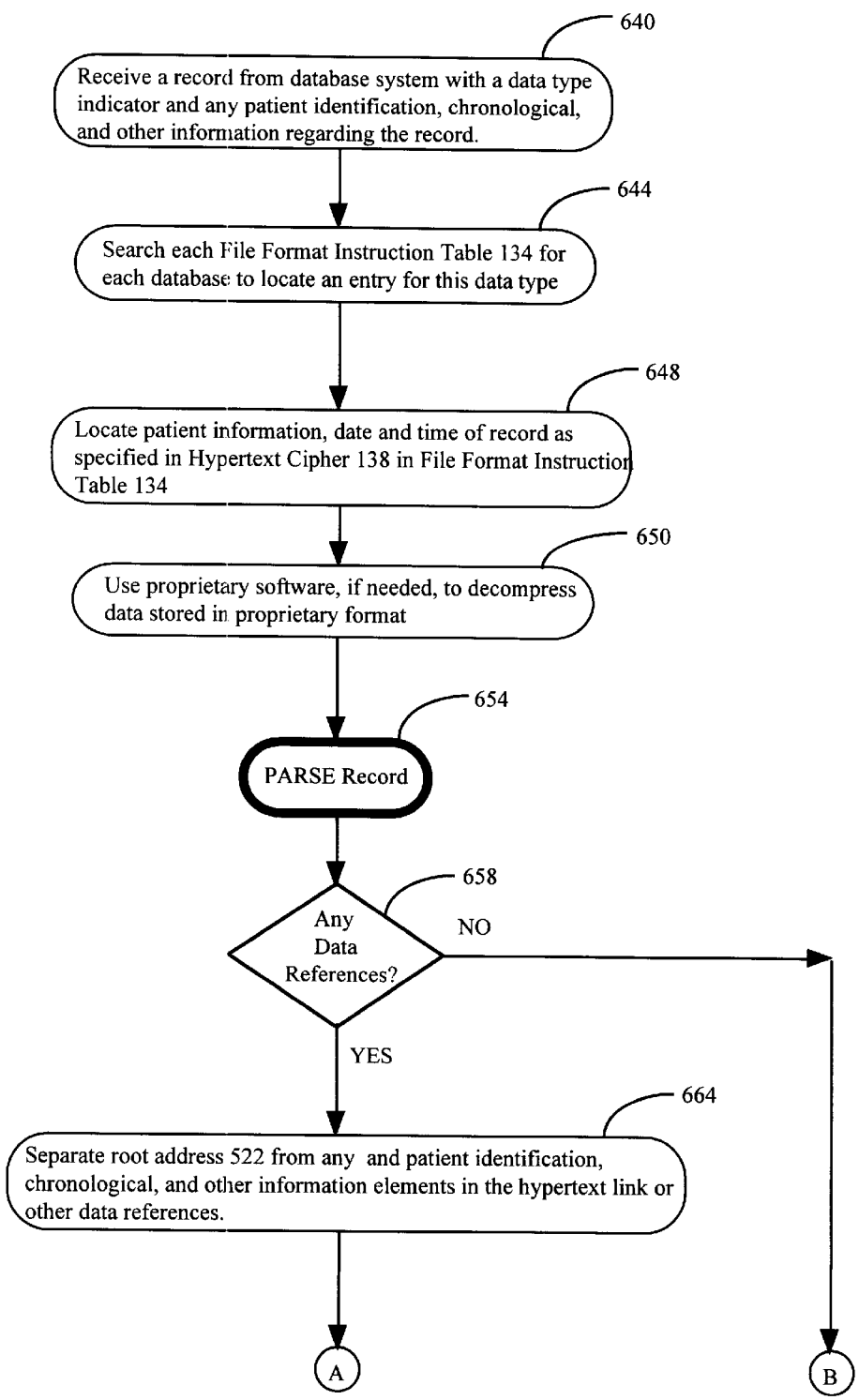
FIGS. 13A–13C are a functional flow chart showing the steps by which the data translation and collection system processes a data record received or retrieved from a workstation or database system on the medical computer network, reformat the data record, assign it a URL address, and deliver it to a database for storage.
Figure 13B:
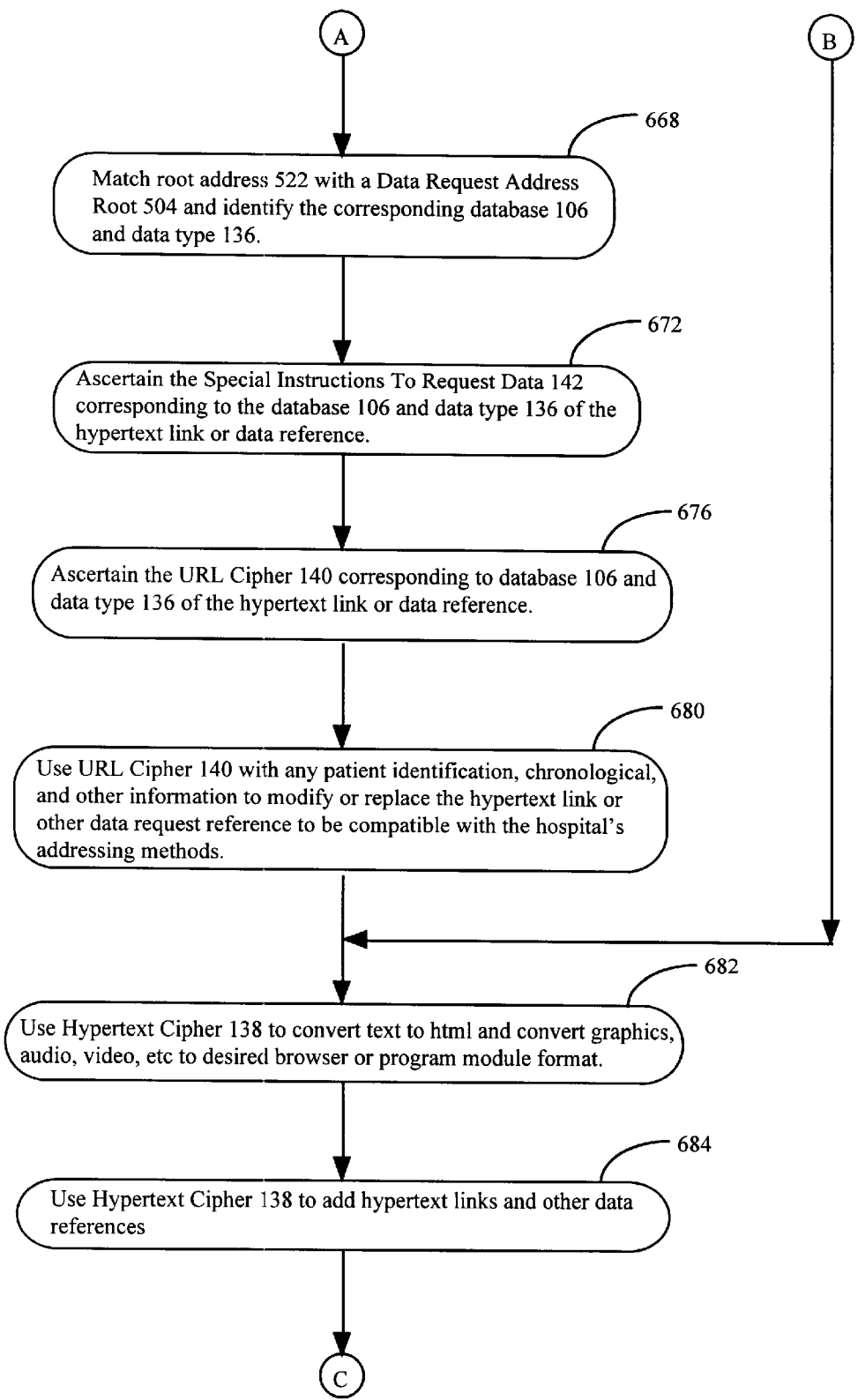
Figure 13C:
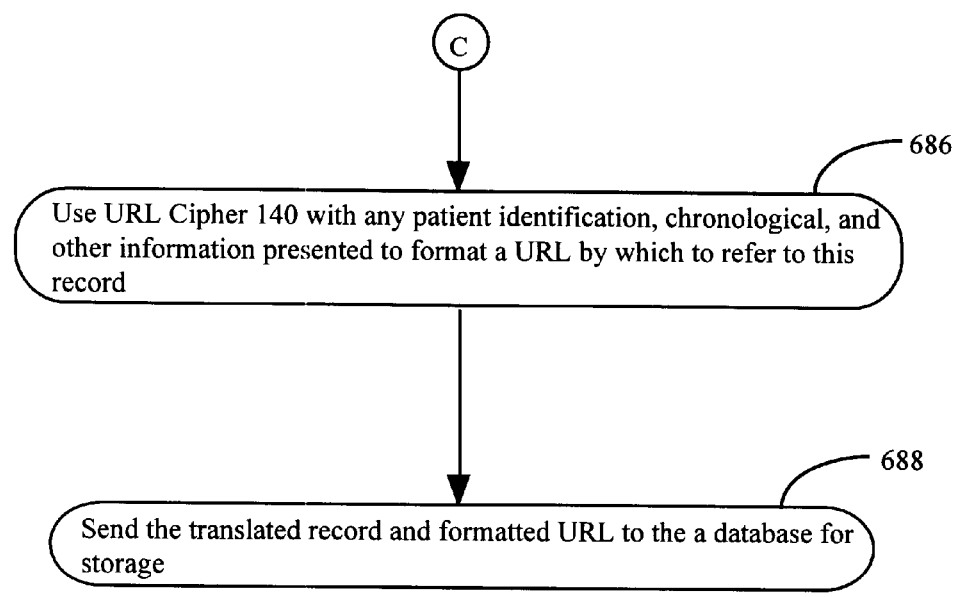

FIGS. 13A–13C set forth an alternate embodiment of the operation of the data translation and collection system 110 (FIG. 1) with particular reference to receiving, translating, and formatting data records to facilitate access through browsers and hypertext links for future users. This embodiment is similar to that set forth in FIGS. 12A–12C but may proceed independently of and prior to a request for such data. Thus in this embodiment the data translation and collection system 110 may serve to organize and format a patient's records prior to their being requested by a member of the medical staff.

Commencing with FIG. 13A, in step 640 the data translation and collection system 110 receives a data record from a database 106 which may include or be appended to other information specifying patient identification, chronological detail, the data type, and other information regarding the record. In step 644, the data translation and collection system searches each File Format Instruction Table 134 (FIG. 3A) corresponding to each entry in Database Register 131 of Database Table 130 to locate the data type 136 of the received data record. In step 648, the hypertext cipher 138 (FIG. 3B) of File Format Instruction Table 134 may be used to parse the record to identify additional information, such as patient information and the date and time of the record.

In step 650, the system uses the hypertext cipher 138 (FIG. 3B) to determine whether or not the data is stored in a proprietary format. If it is, the applicable proprietary software is used to decompress or translate the data. This may be done on the manufacturer's database 106, another computer processing system, or by the data translation and collection system 110 itself.

In step 654, the record is parsed, discussed infra, to locate data references: hypertext links, multi-media requests, and key words or phrases. If none are found, the process advances to step 682, discussed infra.

If hypertext links or references to other data records are found, they may in steps 664 through 680 be reformatted so that the URL addresses are compatible with addressing protocols used by the hospital. In step 664, the root address 522 of the data record reference 520—which may be in the form of a hypertext link—is extracted as in step 544 (FIG. 12A). Similarly, any descriptors 524—such as patient identification, chronological detail, or other non-addressing information—contained in the data record reference 520 is also extracted and temporarily stored. In step 668, a match for this address root is sought among the Data Request Address Roots 504 (FIG. 10) listed in Data Request Catalogue 500 (FIG. 10), which locates the Database 106 (FIG. 10) and Data Type 136 (FIG. 10) corresponding to the matching Data Request Address Root 504. In step 672, the data type 136 and Database 106 identified in step 668 are cross-referenced with their corresponding File Format Instruction Table 134 (FIG. 3A) to locate the special instructions to request data 142 (FIG. 3B). In step 676, the identified Database 106 and Data Type 136 are referenced in Database Table 130 (FIG. 3A) and the corresponding File Format Instruction Table 134 (FIG. 3B) to acquire the appropriate URL cipher 140 (FIG. 3B). In step 680, the URL cipher 140 processes the descriptors 524—the patient identification, chronological detail, and other information—extracted in step 664 to modify or replace the hypertext link or other data reference found in the received data record. Steps 664 through 680 may be performed for each hypertext link and reference to other data records found in the received data record.

In step 682 the data translation and collection system 110, using the Hypertext Cipher 138, converts any text portion of the selected data record into a browser compatible format, such as HTML format, and any graphics, audio, video, or other non-text information into a browser, plug-in, or Java compatible format.

In step 684, the data translation and collection system 110 inserts hypertext links or other references to the received data record in accordance with the hypertext cipher 138 (FIG. 3B) identified in step 548. If directed by the hypertext cipher 138, the record may also be interpreted and modified or reformatted. In step 686, the URL cipher 140 corresponding to the data type 136 (FIG. 3B) of the received data record processes the descriptors 524—the patient identification, chronological detail, and other information stored or extracted in steps 640 or 648—to format a URL by which the received data record may be accessed.

In step 688, the data translation and collection system 110, having translated and formatted the received data record, forwards the record and its formatted URL to an appropriate database 106 for storage.

Figure 14A:
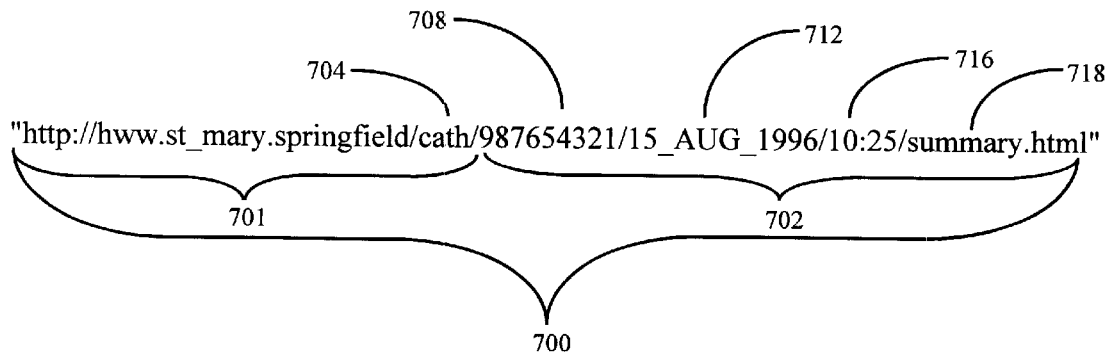
FIGS. 14A–14B are textual representations of a URL address as received and reformatted by the data translation and collection system.

C. Operation of the Hypertext and URL Ciphers of the Data Translation and Collection System FIGS. 14A–14D set forth an example of the hypertext and URL processing performed by the data translation and collection system 110 (FIG. 1) in response to a request for a data record. FIG. 14A proffers, by way of example, a URL address 700 that may be consistent with a standard hospital format, that is received by the data translation and collection system 110. Embedded in this URL address 700 is information regarding the type of data 704, the patient's identification 708, the date 712 and time 716 of the data requested, and a report designator 718. The type of data 704, combined with additional information, is an example of an address root 701 and the information referred to as 708, 712, 716 and 720 are examples of descriptors 702. The data translation and collection system 110, by following steps 544 through 560 as set forth in FIG. 12A, reformats the data request into a new data request 720 (FIG. 14B), which is compatible with the database system 106 (FIG. 1) holding this data.

Figure 14B:
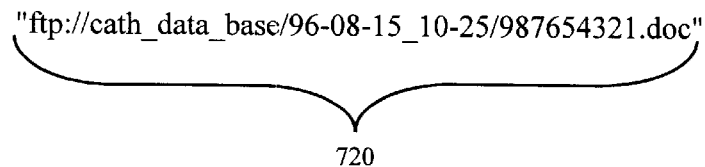
Figure 14C:
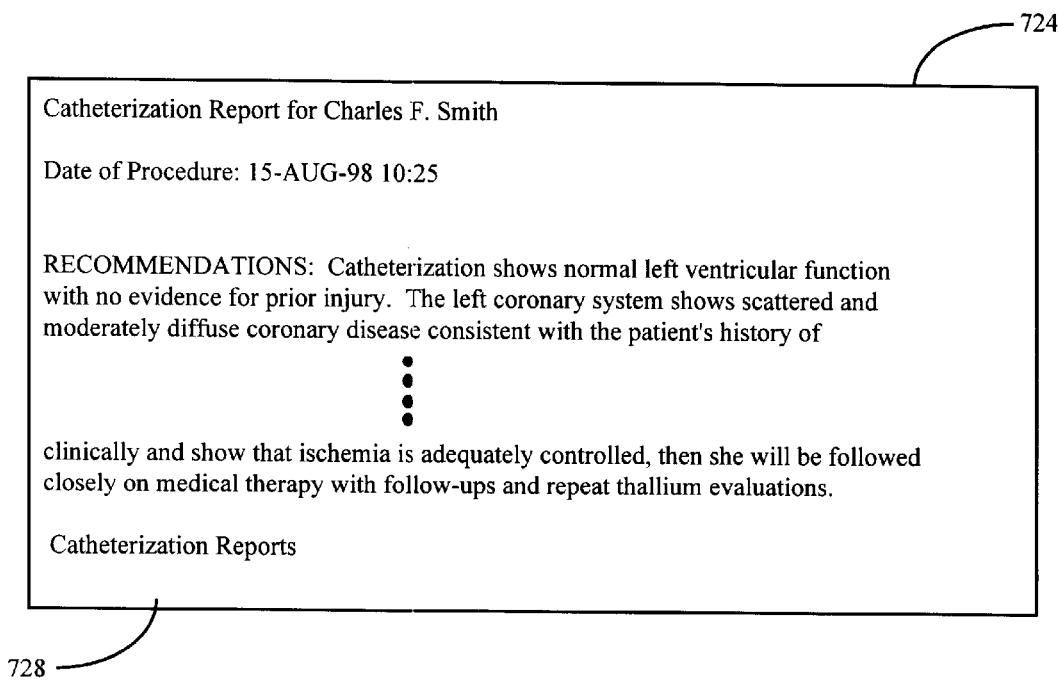
FIG. 14C is a graphical representation of a report referenced by the URL address of FIG. 14B as it would be viewed by a system user through a network browser.
Figure 14D:
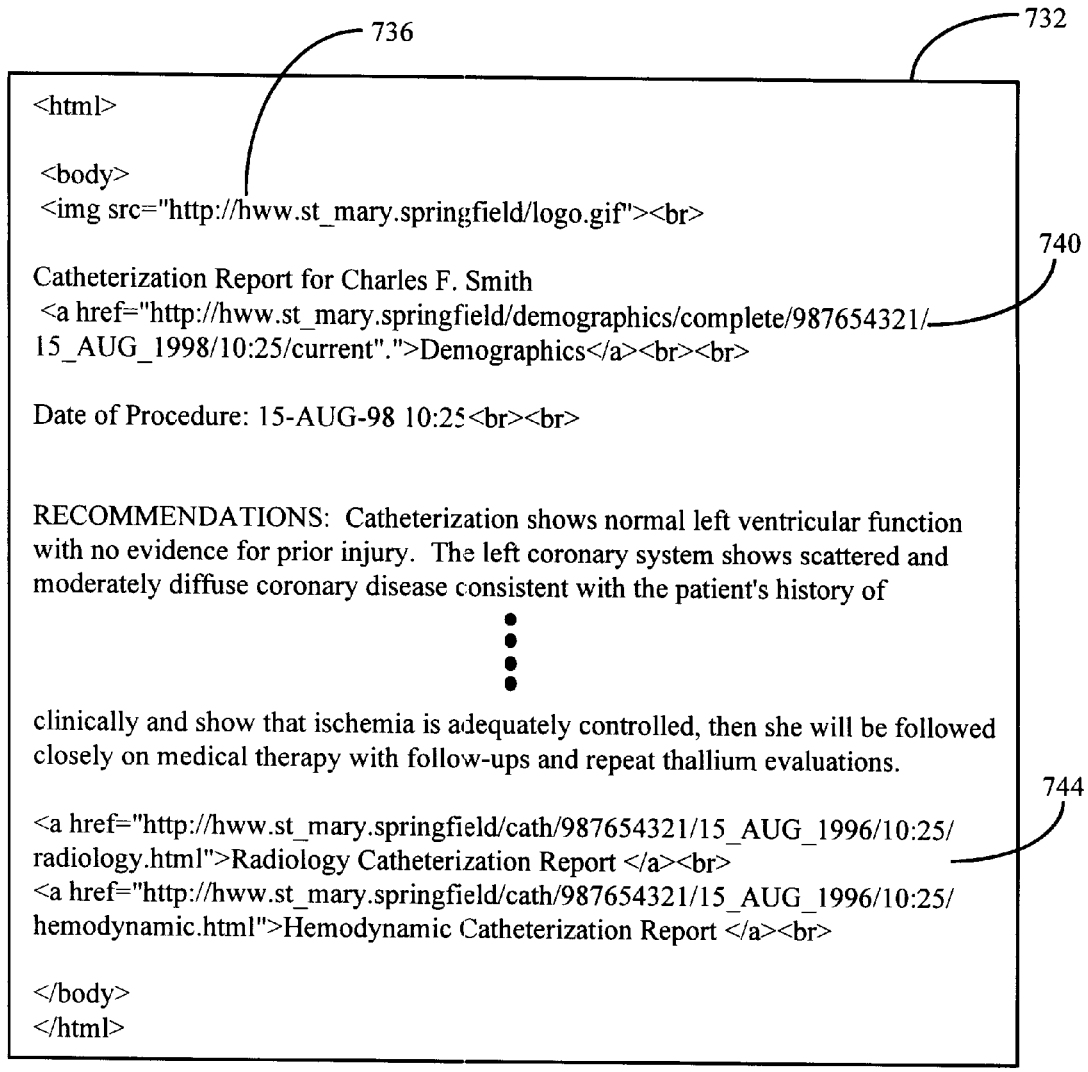
FIG. 14D is a textual representation of the report of FIG. 14C as modified to include data references in the form of HTML codes.

FIG. 14C sets forth an example of a report 724 that may be produced by a database 106 in response to the data request 720 of FIG. 14B. Initially, the report is only a conventional text document. The data translation and collection system 110 (FIG. 1) may then convert the report into an HTML-compatible format 732 (FIG. 14D), inserting data request 736 and hypertext links 740 and 744 according to the hypertext cipher 138 (FIG. 3B). The hypertext links 744 may be inserted based upon the recognition of phrases or special character sequences, such as "Catheterization Reports" 728, in the report, which may vary from report to report of the same data type depending on the each report's contents.

Figure 14E:
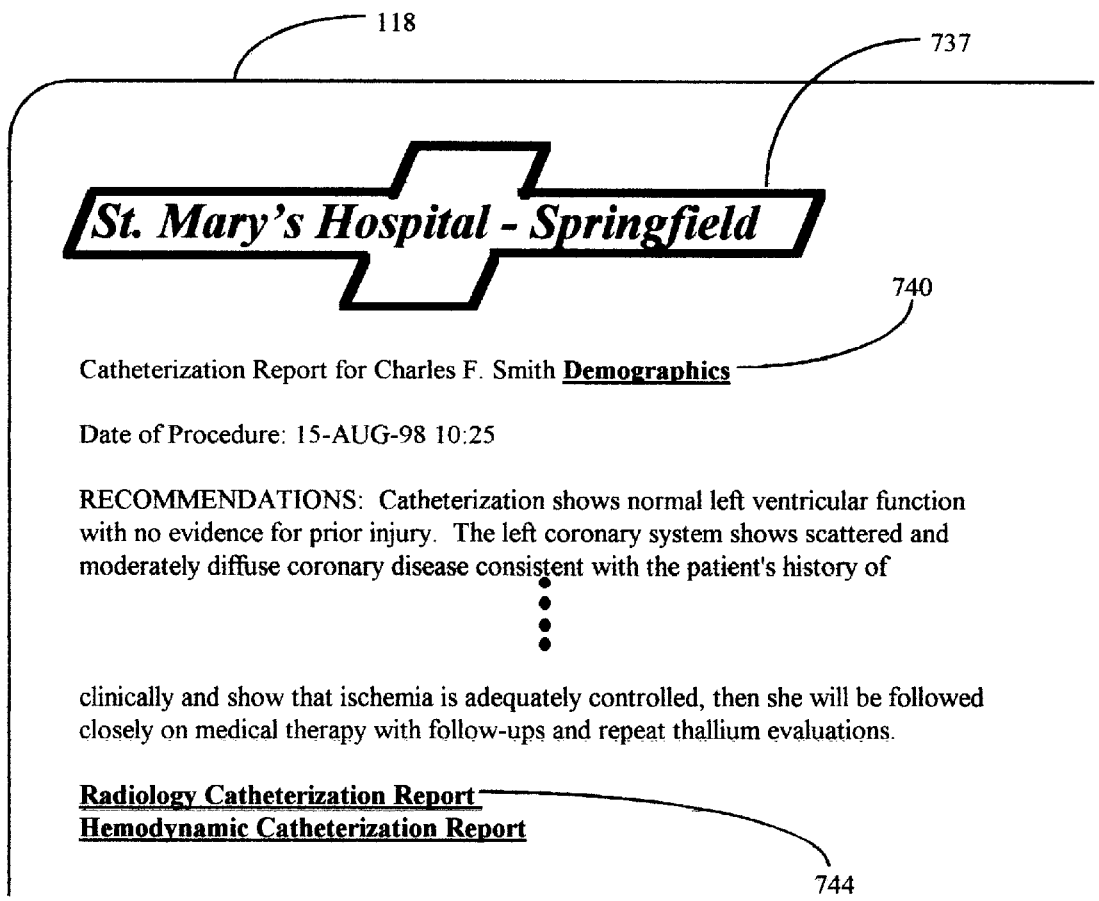
FIG. 14E is a graphical representation of the modified report in FIG. 14D as it would be viewed by a system user through a network browser.

FIG. 14E shows the text report 724 with imported image 737 as displayed on computer display 118 using a network browser software package after the report has been translated and modified. A system user seeking additional information regarding the patient's demographics could select hypertext link 740. A system user seeking either the radiology or hemodynamic report for this procedure could select the appropriate hypertext link 744.

D. Data Collection and Translation for Storage and Retrieval

FIGS. 5A–5E set forth a second alternate embodiment of the operation of the data translation and collection system 110 (FIG. 1) with particular reference to the steps used by the data translation and collection system 110 to retrieve and format data to produce a complete, organized, hypertext-linked, and browser-compatible collection of records pertaining to a person, place, thing, or event. This operation may be initiated by a system user executing the appropriate command or may be executed routinely and automatically by the hospital's Admit, Discharge, and Transfer (ADT) system or Hospital Information System (HIS) during a patient's stay or when a patient is discharged.

In step 200, the data translation and collection system 110 (FIG. 1) receives a patient identification number, which may originate from a staffed workstation 102 (FIG. 1) or automatically from the ADT system 108 (FIG. 1) or HIS 111 (FIG. 1). This may be done, for example, when a patient is admitted or after one has been discharged. In step 204, the data translation and collection system 110 may request the dates for which the system user desires to collect data for the patient or the most recent admission dates from the ADT system 108 or HIS 111. In step 208, a file containing a list of received records will be opened, if previously created, or generated, if not previously created. Similarly, in step 212, a file containing a list of records to be retrieved is opened, if previously created, or generated, if not previously created. In step 216, the data translation and collection system 110 references database table 130 (FIG. 3A) to locate and retrieve the first database entry in the database register 131 (FIG. 3A), the corresponding File Format Instruction table 134 (FIGS. 3A and 3B) and the first data type 136 (FIG. 3B) in the File Format Instruction table 134.

Steps 220 through 276 set forth an iterative search of all the databases 106 (FIG. 1) on the medical computer network 100 (FIG. 1) to collect, translate, and format all records relevant to a patient's medical history.

In step 220, the field containing special instructions to request data 142 (FIG. 3B) corresponding to the data type 136 (FIG. 3B) being referenced by the data translation and collection system 110 is used to construct and format a message which is sent, using address 132 (FIG. 3A), to the database 106 being referenced in database register 131 (FIG. 3A). This message may incorporate passwords, macros, or other codes, as necessary, to retrieve the data. In step 224 a data record is retrieved.

In step 226, the record is parsed per the Hypertext Cipher 138 (FIG. 3B) in the File Format Instruction Table 134 (FIG. 3B) to derive the date and time of the record. In step 228 the file name is added to the list of received records opened in step 208. In step 232, the list of records to retrieve opened in step 212 is checked for a reference to the retrieved record. If a reference exists, in step 236 it is removed from the list of records to retrieve.

In step 240, the system uses the Hypertext Cipher 138 (FIG. 3B) to determine whether or not the data is stored in a proprietary format. If it is, the applicable proprietary software is used to decompress or translate the data. This may be done on the manufacturer's database 106, another computer processing system, or by the data translation and collection system 110 itself.

In step 246, the record is parsed, discussed infra, to locate data references: hypertext links, multi-media requests, and key words or phrases. If none are found, the process advances to step 266, discussed infra if there are data references, a check is made to determine if the data being referenced had been located previously (step 254). If it had not been previously located, the record is added to the List of Records to Retrieve (step 258). In step 262, all hypertext links and other data requests are reformatted through use of the URL Ciphers 140, maintained by the data translation and collection system 110 for each Data Type 136. This is done in a manner similar to steps 580 to 596, discussed supra. Thus when the retrieved data record is later displayed, secondary files referenced by it will be included for display and the system user will not be presented an incomplete record.

In step 266, whether there were data references or not, Hypertext Cipher 138 is used to convert text to HTML format, graphics, audio, video, or other non-text information into a browser, plug-in, or Java compatible format.

While not shown in the flow chart of FIGS. 5A–5E, if the data translation and collection system 110 retrieves a record that includes a program code module such as a Java applet, the data translation and collection system will attempt to retrieve a copy of the applet from an address specified by the applet program code, generate a new address for the applet copy which will be stored with the patient's data record collection, and modify the program code module to reflect the new address. Similarly, if the data translation and collection system 110 retrieves a record that requires a browser extension or "plug-in" in order to be properly viewed, a copy of the applicable extension or "plug-in" is also retrieved for storage with the patient's data record collection.

For purposes of privacy or security, the medical computer network 100 may deny access to some data records in the list of records to be retrieved. In such instances a substitute file, indicating that the requested file is confidential or has not been included, is created and stored, and its reference substituted for the reference to the confidential data record.

In step 268, a retrieved data record may be further modified, such as by inserting additional hypertext links or data requests to the record per the hypertext cipher 138 (FIG. 3B). Also, the URL cipher 140 corresponding to the data type 136 (FIG. 3B) of the retrieved data record is used to format a URL by which the retrieved data record may be accessed. Further, the data translation and collection system 110 creates and opens an appropriate file folder and file to store the converted retrieved record as specified by the URL cipher 140 field.

In step 276, the File Format Instruction Table 134 (FIG. 3B) for the instant database is checked to determine if additional data types 136 are available. If so, in step 272 the process of steps 220 through 276 is repeated for the next data type 136. If the search has been performed for each data type in the instant database, the search proceeds to the next database indicated in database register 131 (FIG. 3A), starting with its first data type 136 and proceeding, in similar fashion, through each of its data types 136, until the search has been performed for every data type 136 of every database in database table 130 (FIG. 3A). The procedure progresses to step 284 after completing this search through the registered databases.

In step 284, the list of records to retrieve opened in step 212 is examined for the existence of records or program modules that have not yet been retrieved. If the list is empty, the data collection for the patient has been completed and the process advances to step 324 (FIG. 5E), discussed infra. If the list is not empty, in step 288 a request is sent for the first entry remaining in the list, which may be for a data record or a program module. If it is a data record, after it is retrieved, it is checked in step 290 for encryption and decoded, if necessary, using proprietary software.

On step 298, the record is parsed, discussed infra, to locate data references: hypertex links, multi-media requests, and key words or phrases. If none are found, the process advances to step 314, discussed infra if there are data references a check is made to determine if the data being referenced had been located previously (step 302). If it had not been previously located, the record is added to the List of Records to Retrieve (step 306). On step 310, all hypertext links and other data requests are reformatted through use of the URL Ciphers 140, maintained by the data translation and collection system 110 for each data type 136. This way, the URL or other data request addresses are compatible with the addressing convention to be used on the storage medium to which the records will be written. When the retrieved data record is later displayed through a network browser, secondary files referenced by the retrieved data record are made easily and quickly accessible to the system user with the click of a mouse.

In step 314, whether there were data references or not, Hypertex Cipher 138 is used to convert text to HTML format, graphics, audio, video, or other non-text information into a browser, plug-in, or Java compatible format.

In step 316, the data translation and collection system 110 creates and opens an appropriate file folder and file to store the converted retrieved record, either as specified by the URL cipher 140 field (FIG. 3B) (if the retrieved record is part of the patient's file), or with a distinctive file name (if the retrieved record is not part of the patient's file, e.g., a physician's biographical background). In step 320, the retrieved record or program module, as it may be, is removed from the list of records to retrieve, and steps 284 through 320 are repeated until the list is empty.

E. Workstation Data Collection and Translation

The operation of the data translation and collection system 110 (FIG. 1) set forth in FIGS. 5A–5E may be initiated in other ways. In one mode of operation, the databases 106 (FIG. 1) on the hospital's communication network 112 may send data for each patient to the data translation and collection system 110 periodically or after the patient is discharged. In another mode of operation, the workstations 102 on the hospital's communication network 112 may send reports, such as those produced by word processors, to the data translation and collection system for translation and storage. In yet another mode of operation, the data translation and collection system may have access to a drive, directory, or folder on one or more of the workstations 102 residing on the communication network, from which it may search and retrieve data records.

System users such as physicians often produce reports, such as word processing files, on their own workstations 102 or 104 (FIG. 1) that are relevant to a patient's condition, status, or profile, and which merit inclusion in the data translation and collection system 110 of the present invention. This need may be accommodated by placing any report that is to be retrieved by the data translation and collection system 110 in a special folder 105 named "Collection." The data translation and collection system 110 may maintain a file containing a Workstation Data Table 150, as set forth in FIG. 4A, which includes the addresses 152 of all workstations 102 and physician office workstations 104 and file access commands 154 or passwords used to gain access to files stored in each workstation's "Collection" folder 105. The data translation and collection system 110 may also maintain a Workstation File Formatting Instruction Table 158, as set forth in FIG. 4B, which includes each report name and corresponding file name and data formatting instructions 162 and Workstation URL cipher 166.

On a periodic basis or as instructed, a program in the data translation and collection system 110 (FIG. 1) may determine if there are any files in the special "Collection" folder 105 in each workstation 102, 104. If any files exist, the file access commands 154 (FIG. 4A) may be sent to the workstation so that the files may be transferred to the data translation and collection system 110. This may be done using the file transfer protocol, FTP, of the Internet/Intranet or by other data transfer methods.

If the user of the workstation 102, 104 creates reports, that when stored use a file name formatted according to file name and data formatting instructions 162 (FIG. 4B), the file may be recognized as being a specific file for a patient. For example, the file named "Cath987654321" may correspond to a catheterization report for the patient whose identification number is 987654321. Appending the date and time to the file name may be used to further identify the report. Alternatively, file name and formatting instructions 162 may require that the date and time be located within the report itself. Similarly, the report name and/or the patient's identification information may be incorporated in the report or its file name. In either case, once the file and its file name are received and recognized, the file may be processed in the same manner that data records retrieved from databases are processed as set forth in FIGS. 5A–5E, but using the Workstation Data Table 150 and its Workstation File Formatting Instruction Tables 158 in place of the Database Table 130 and its File Formatting Instruction Tables 134.

Instruments or medical devices whose reports are not stored as part of any database 106 (FIG. 1), but that are capable of writing data to a floppy disk or transmitting information via an infrared or serial line connection to a workstation 102, 104 may also store patient reports in the data translation and collection system 110. To do so, the individual reports may be written to a floppy disk using any file name defined by the file name and data formatting instructions 162 (FIG. 4B). The reports may be copied manually or automatically from the floppy in workstation 102, 104 to the "Collection" folder 105, which may be periodically checked to see if there is any data in it to be retrieved, or the reports may be automatically read by the workstation and sent to the data translation and collection system 110. The reports so sent may be incorporated with any others received for this patient and may be provided with a new destination file according to the Workstation URL Cipher 166.

In this manner reports from word processors or from mobile medical devices may be collected for display and storage and may be assigned structured file names to assist in their retrieval whether on line or when placed on line as with a CD-ROM device 117 (FIG. 2).

F. Creation, Structuring, and Mass-Media Storage of Patient Data

Figure 5A:
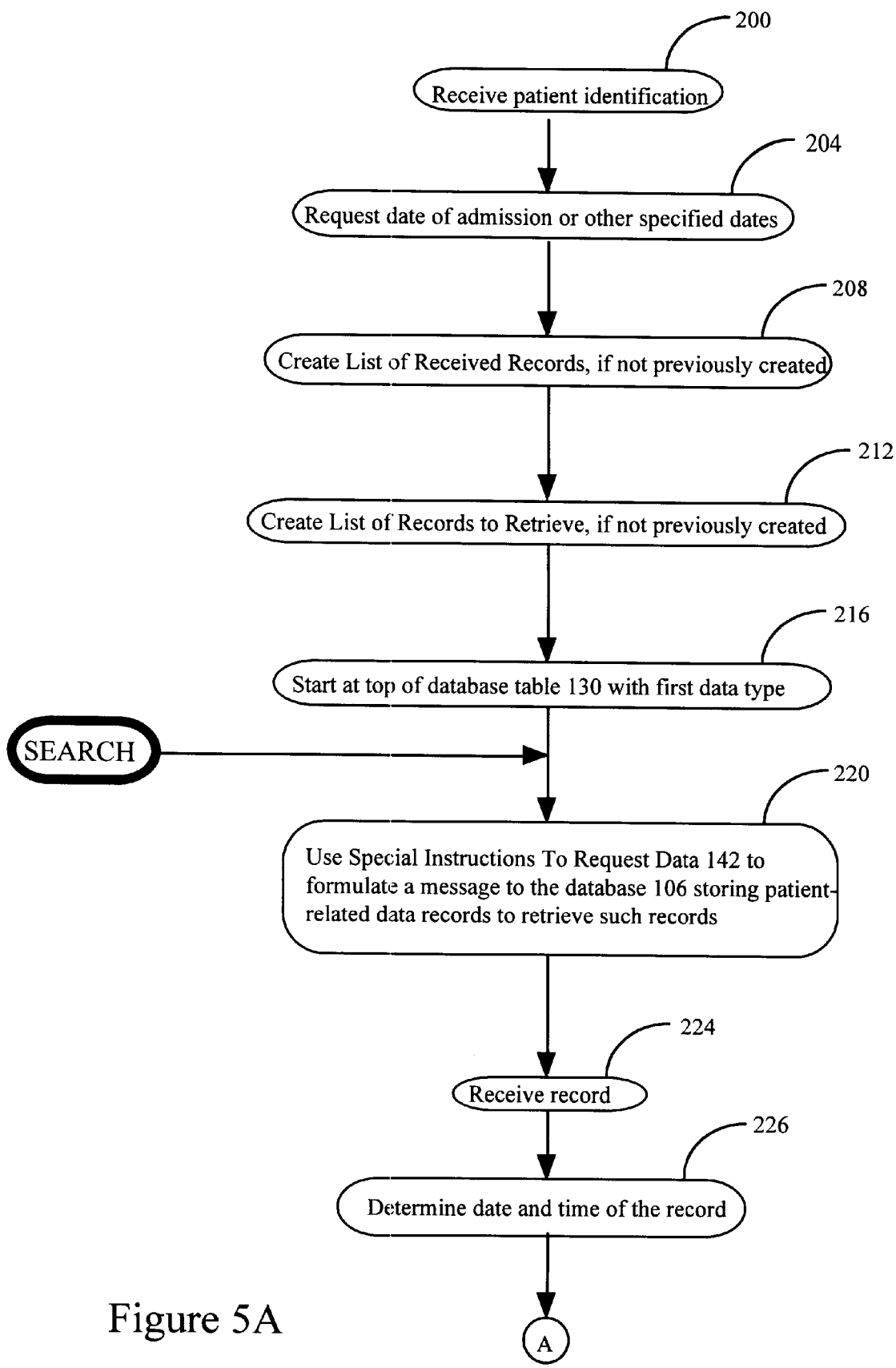
FIGS. 5A–5F are functional flow charts showing the steps used to collect and process a related set of data records from various databases, create a structured set of control files containing hypertext links to the collected data records, and store the data records and control files to a storage device.
Figure 5B:
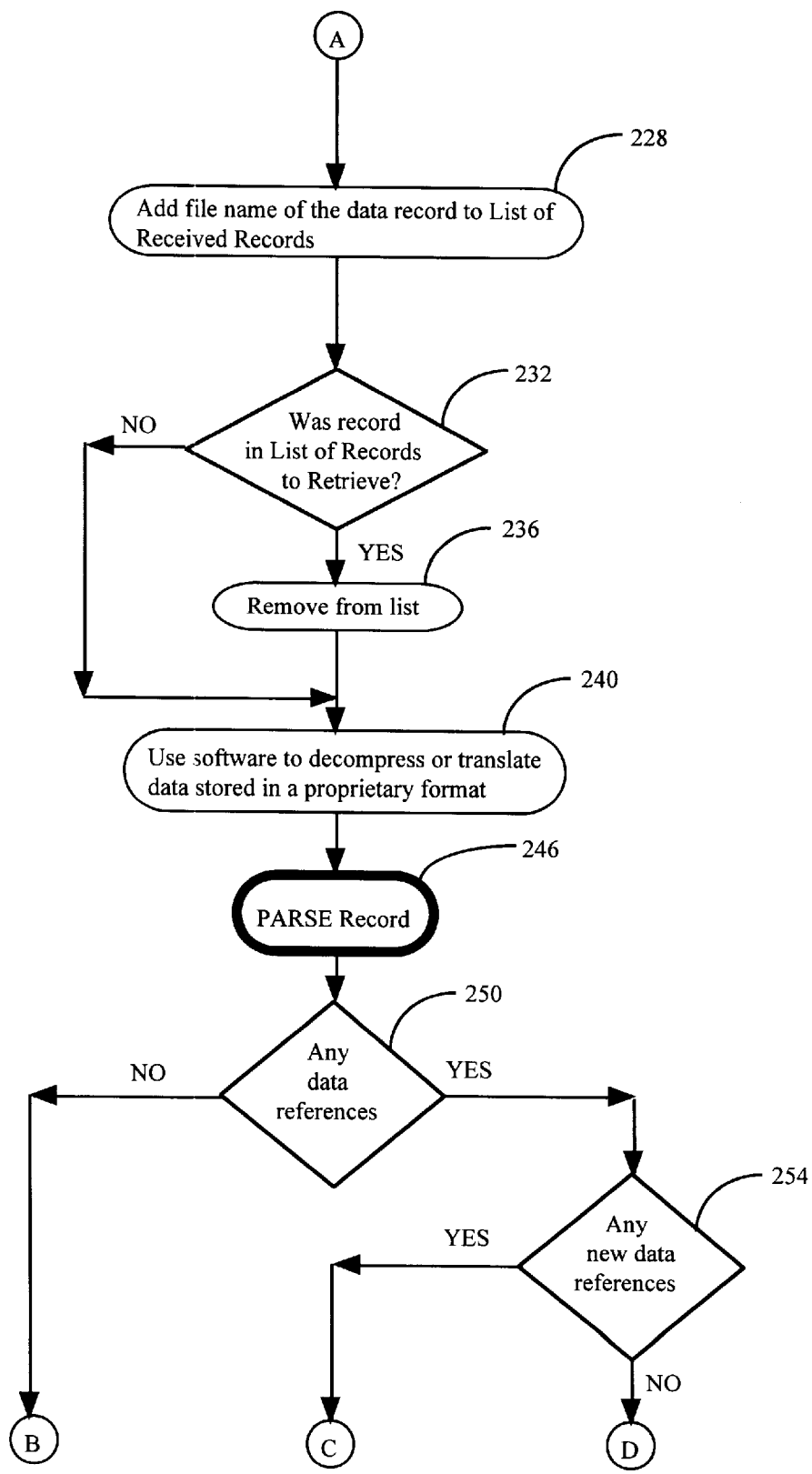
Figure 5C:
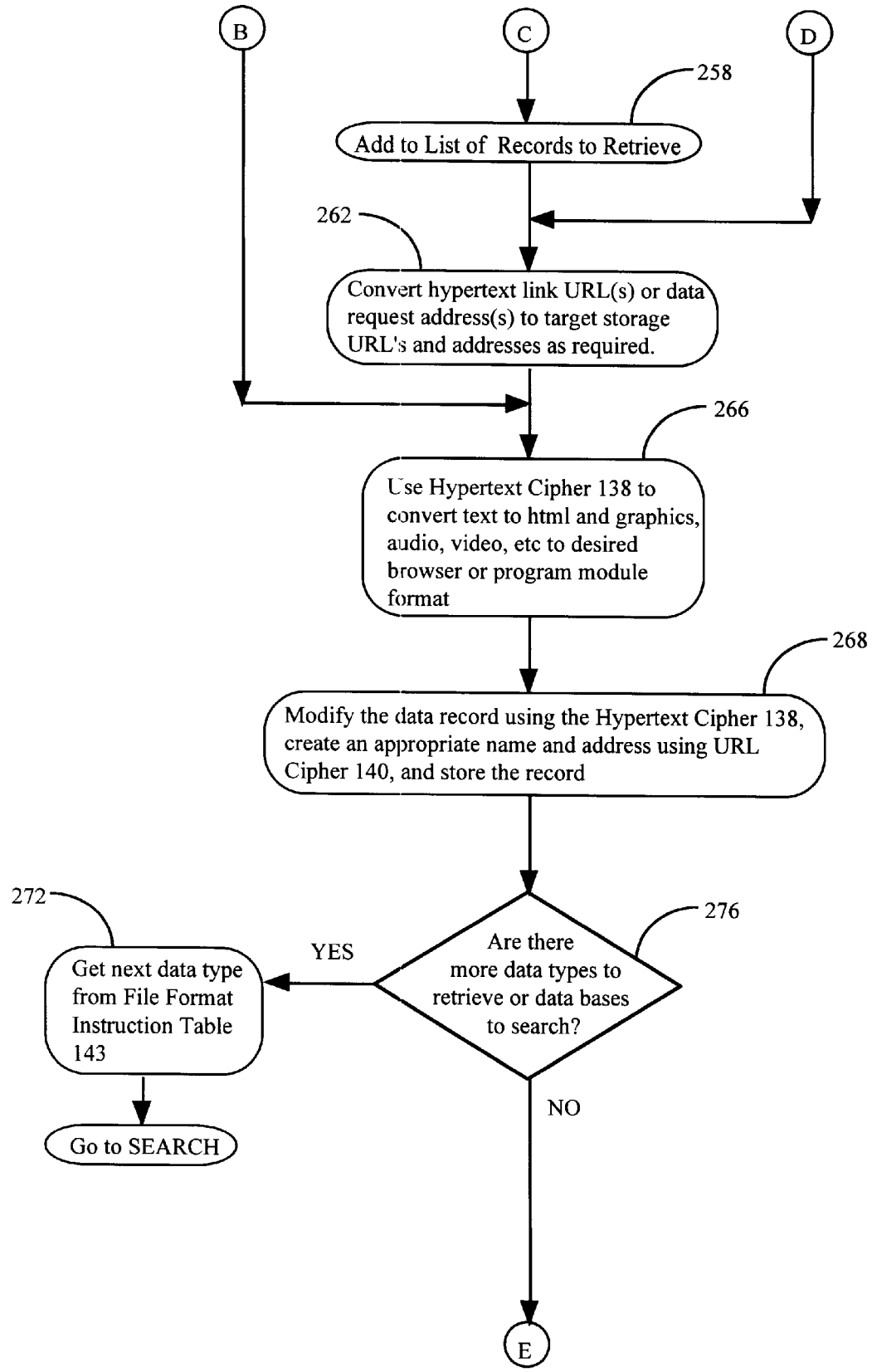
Figure 5D:
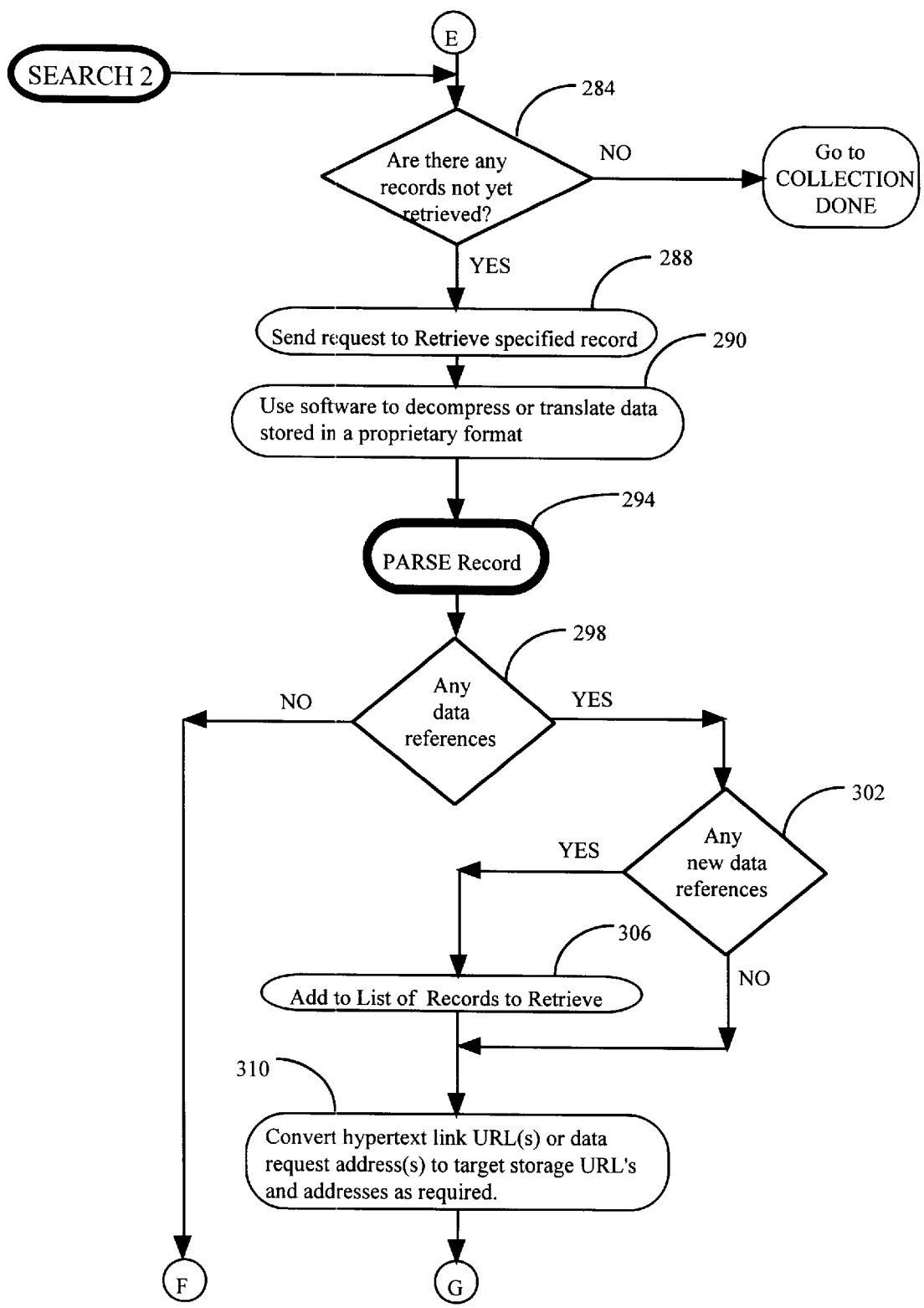
Figure 5E:
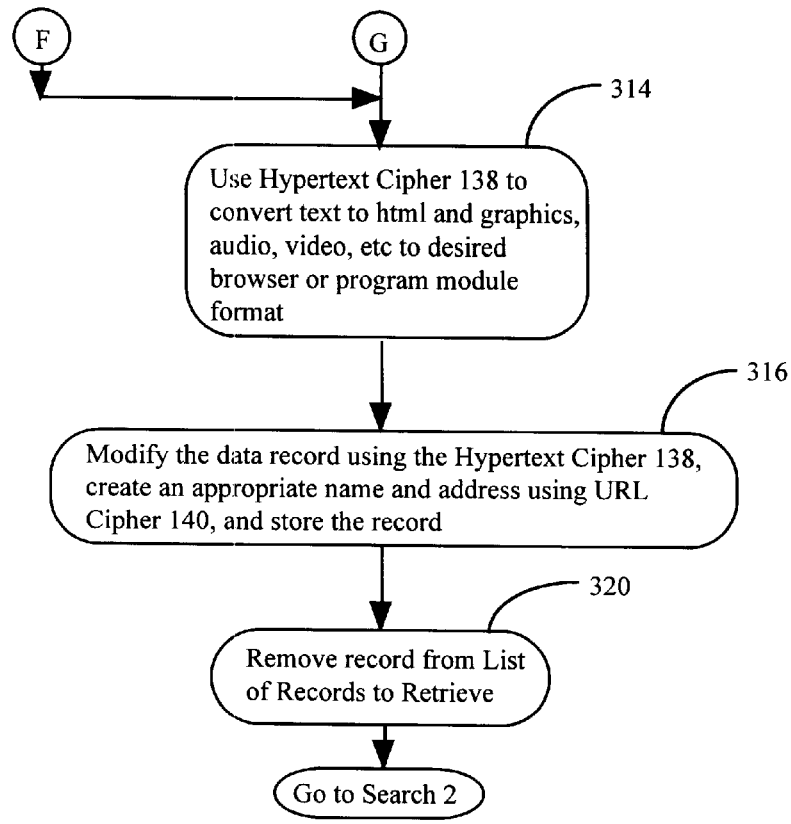
Figure 5F:
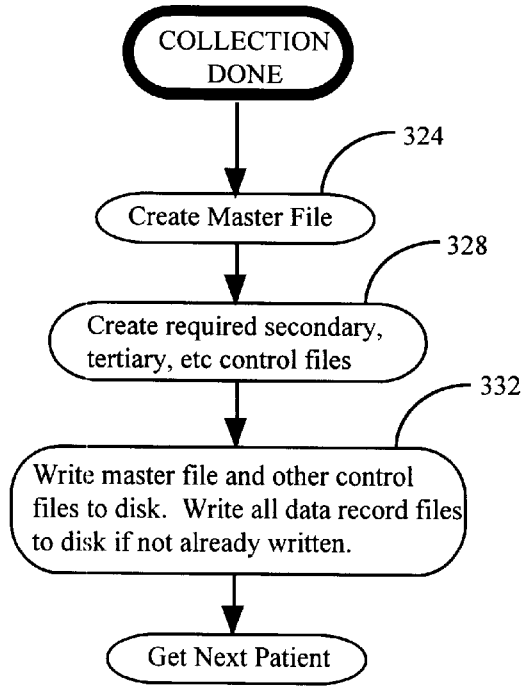

Commencing with step 324, FIG. 5F sets forth the process by which a patient's many data records may be stored on a mass storage device. In step 324, a master file 400 (FIG. 6A) is created as data records are received or when an the data records have been retrieved. The master file name may be based on the patient's name or identification number. In some cases it may be desirable to create the same file twice, using the patient's name for the file name once and the patient's identification number for the other. In step 328, secondary, tertiary, or other subdominant control files 418 (FIG. 8A) may also be created. A "master" file is roughly analogous to a root directory or a home page on a website, for through this single file and the patient's data records may be accessed through hypertext links. While a "master" file may contain text, graphics, video, or audio, it contains a list of links to other reports—for example, the discharge report link 408 (FIG. 6B) to discharge report 412 (FIG. 7A)—or links to other "control" files—for example, the cardiology link 404 to cardiology control file 418 (FIG. 8A). "Control" files are roughly analogous to subdirectories. Although they incorporate text, graphics, or other multimedia features, they serve primarily to present an organized collection of links to related patient records.

The URL Cipher 140 corresponding to the date type 136 of each data record retrieved, can be used to determine whether a hypertext link to retrieve the data record from the mass storage device is to be placed in a master, secondary, or tertiary control file.

In step 332, the master and control files are written to a mass storage device along wish the data records if they have not been previously been written to the mass storage device. A CD-ROM disk that has a patient's data written to it may be given to appropriate physicians for their own storage and use. To view the contents of the CD-ROM, a physician would need only to insert it into the CD-ROM drive 117 (FIG. 2) of a physician workstation 104 (FIG. 1) and run a network browser program. By using the File command the physician could refer to the CD-ROM drive 117, which would list the name of the master file 400, which may be the same or similar to the patient's name.

FIG. 6A sets forth an example of the contents of the master file 400. Besides identifying the patient and the dates and source of the medical records, the master file has a series of hypertext links 402 either to distinct reports, such as hypertext link 408, or to secondary control files, such as hypertext link 404. FIG. 6B sets forth how master file 400 (FIG. 6A) might appear through a browser program when presented on display 118. Note that hypertext links 402 are displayed in a different font format, as is the convention with browser programs. The system user may select a hypertext link by moving a pointing device such as a mouse over the text and pressing an activation button. The browser will automatically retrieve the file specified in the hypertext link 402 from the CD-ROM and present it.

If the system user selects the hypertext link 408 specifying discharge report in the master file 400, the system user will be presented with the patient's single discharge report 412 (FIG. 7A). FIG. 7A sets forth some of the HTML codes which may be used to format discharge report 412. Hypertext link 416 may be selected to retrieve the specified catheterization report from the CD-ROM. The hypertext link URL address has been modified as needed to make it compatible with the storage structure of the CD-ROM. FIG. 7B sets forth how discharge report 412 (FIG. 7A) might appear through a browser program when presented on display a 118.

FIG. 8A sets forth the contents of a secondary control file 418 that a browser program would present if the system user, while viewing master file 400 (FIG. 6A), selected the hypertext link 404 specifying cardiology data. Secondary control file 418 presents the system user with various types of cardiology reports to choose from in the form of hypertext links 422. For those cardiology tests for which there is only one report available, the hypertext link specifies the URL address of that report. For those tests for which there are several reports available, the hypertext link 420 may specify the URL of a tertiary control file. FIG. 8B sets forth how secondary control file 418 (FIG. 8A) might appear through a browser program when presented on display 118.

FIG. 9A sets forth the contents of tertiary control file 424 that a browser program would present if the system user, while viewing secondary control file 418 (FIG. 8B), selected the hypertext link 420 specifying electrocardiograph reports. This file presents the system user with a list of all the electrocardiograph reports, during the dates selected, to choose from in the form of hypertext links 426. For each electrocardiograph report the hypertext link specifies the URL address of the report. FIG. 9B sets forth how tertiary control file 424 (FIG. 9A) and its list of electrocardiograph reports might appear through a browser program when presented on display 118.

G. Parsing to Locate Data References

Figure 15A:
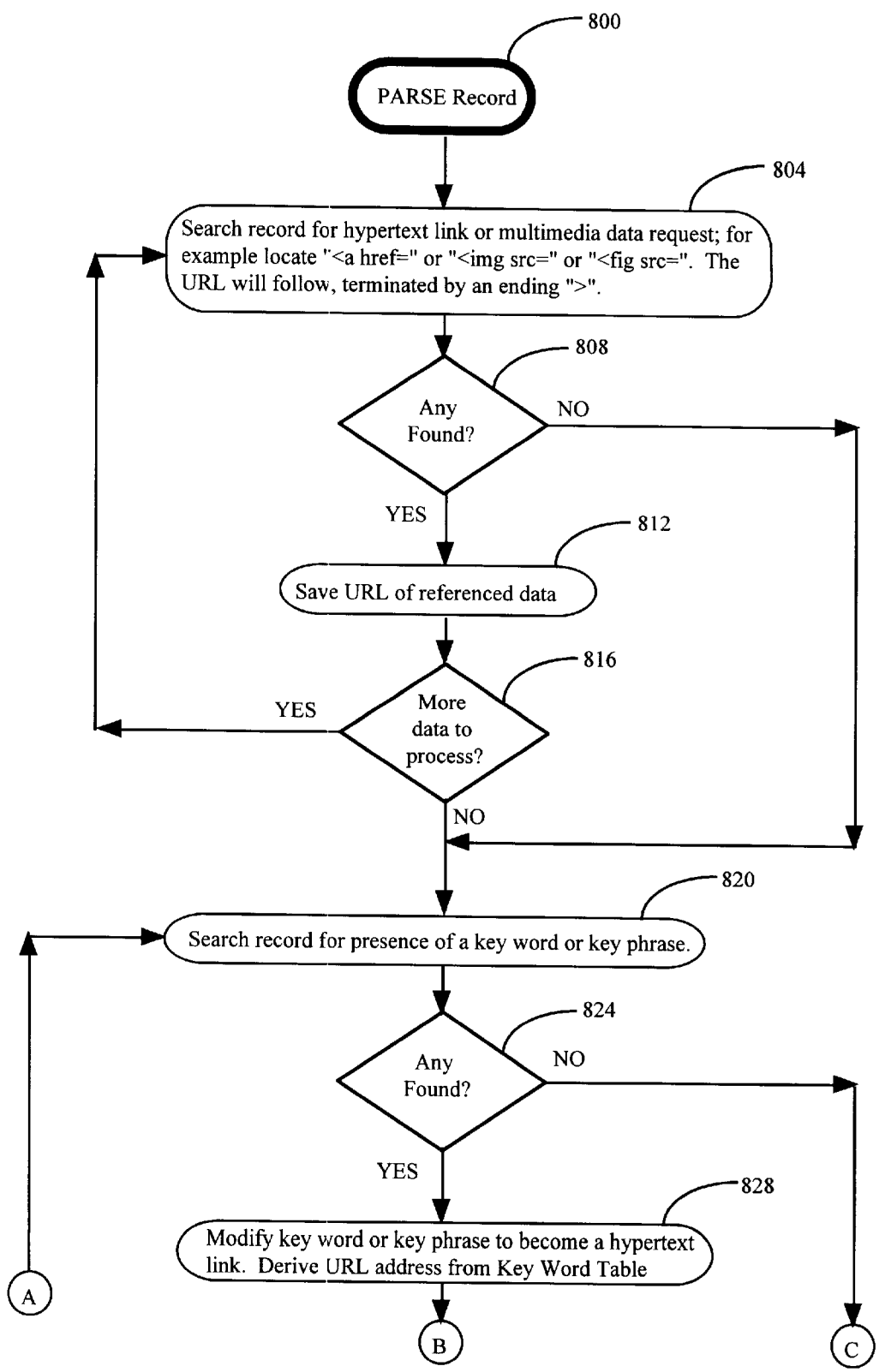
FIGS. 15A–15B are a functional flow chart showing the steps by which a data record is parsed to locate data references within it.
Figure 15B:
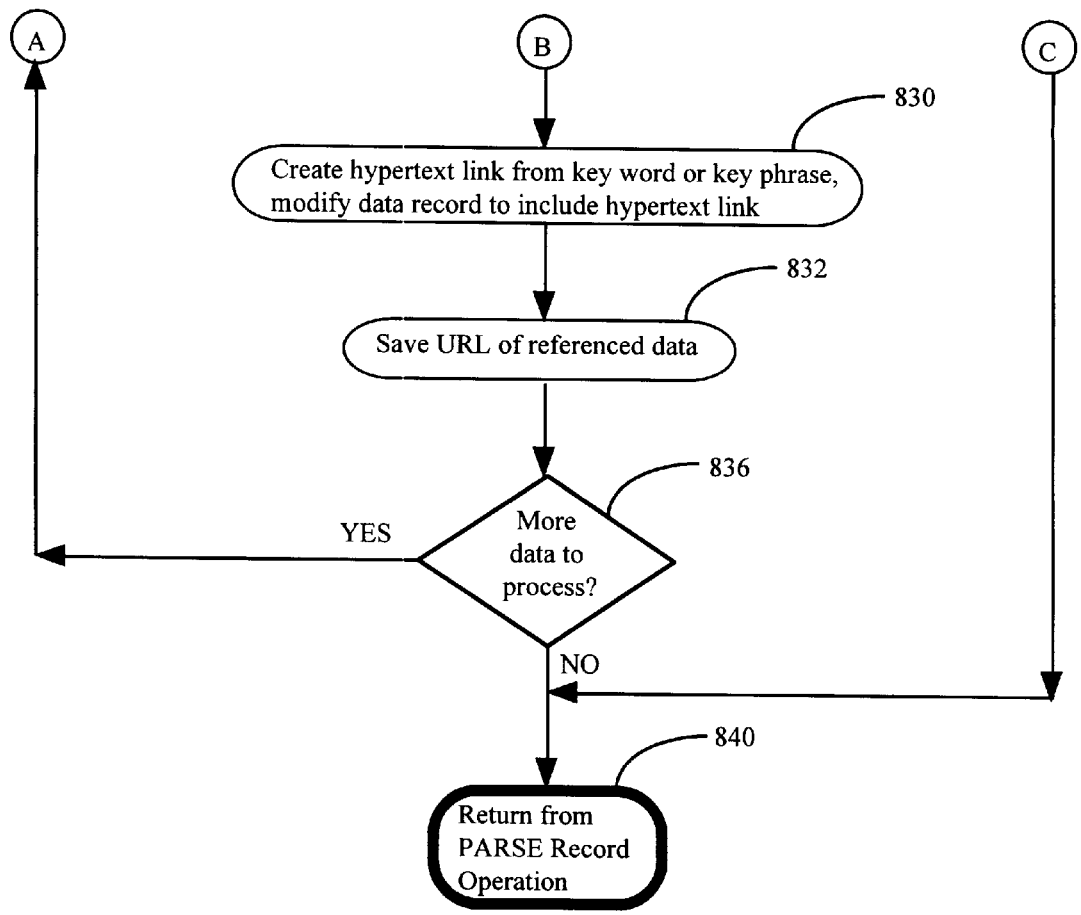

FIG. 15A illustrates how a data record is parsed. A data record is parsed to locate data references by searching it for text corresponding to a hypertext link or a multimedia data request. If one is found, the URL is located after the initial control sequence and will be saved (step 812) for use after the parsing is completed. If none are found, or when the record has been completely parsed, another pass can be made to search for data references in the form of key words or key phrases (step 820).

A key word or phrase is a recognized text string that is to be converted into a hypertext link. As an example, the data reference indicated by the phrase, "Admission ECG," can be converted (steps 828, 830) into the following hypertext link:

<a href="hww.st_mary.springfield/ecg/987654321/ 03may1997/ecg/admission.html">Admission ECG</a>.

The expression "03may1997" is the date the data record being parsed was created. The patient ID (987654321), the date, and other descriptors are available from steps 200 and 226, or from steps 544 or 560. A wide variety of medical expressions can be recognized as key words or phrases, and appropriate hypertext links created from them. The URL of the hyperlink is saved for later use (step 832). When the entire record has been searched (step 836), the URLs of the located data references are returned to the section of the flow chart that requested the record to be parsed (step 840).

While a particular embodiment of the invention has been illustrated and described, it will be obvious to those skilled in the art that various changes and modifications may be made without sacrificing the advantages provided by the principle of construction disclosed herein.

What is claimed is:

1. A computer system with a plurality of data records on a plurality of databases, and a standardized format for addressing said data records, said computer system comprising:

(a) a user interface having an interactive display program for requesting one of said data records and displaying a plurality of interface supported data formats;

(b) means for receiving a reference to a first data record from said interactive display program;

(c) means for retrieving said first data record;

(d) means for parsing said first data record to identify a reference to a second data record;

(e) means for modifying said reference to said second data record to create an address, said address being operable to retrieve said second data record; and (f) means for sending said modified first data record to said interactive display program.

2. The computer system of claim 1, wherein said reference to said second data record comprises a hypertext link.

3. The computer system of claim 2, wherein said address is created by using information determined by parsing said reference to said first data record.

4. The computer system of claim 3, wherein said address is a hyperlink using said standardized addresses for addressing said second data record.

5. The computer system of claim 4, wherein said first data record is converted from a format not supported by said display program to one that is supported by said display program.

6. The computer system of claim 5, wherein the computer system is a hospital medical system.

7. The computer system of claim 1, wherein said reference to said second data record comprises a keyword phrase.

8. The computer system of claim 7, wherein said address is created by using information determined by parsing said reference to said first data record.

9. The computer system of claim 8, wherein said address is a hyperlink using said standardized addresses for addressing said second data record.

10. The computer system of claim 9, wherein the computer system is a hospital medical system.

11. The computer system of claim 10, wherein said first data record is converted from a format not supported by said display program to one that is supported by said display program.

12. A computer system for converting a plurality of data references within a plurality of data records on a plurality of databases into hypertext links using standardized addresses, the computer system comprising:

(a) a user interface having an interactive display program for displaying a plurality of interface supported data formats;

(b) means for receiving a first reference to a group of related data records from an accessory computer system;

(c) a list of data types stored on each said database, and a list of instructions to retrieve each data record of said data types;

(d) means for retrieving said group of related data records using information in said first reference;

(e) means for parsing each of said group of related data records to identify a second reference to a second data record;

(f) means for modifying each occurrence of said second reference in each data record of said group of related data records to create a first address, wherein said first address is operable to retrieve said second data record;

(g) means for retrieving said second data record;

(h) means for parsing said second record to identify a third reference to a third data record; and (i) means for modifying said third reference to create a second address, wherein said second address is operable to retrieve said third data record.

13. The computer system of claim 12, further comprising:

means for recursively locating additional references to additional data records; and means for modifying said additional references to create additional addresses, wherein each said additional address is operable to retrieve a specific one of said additional data records, thereby establishing a modified group of related data records associated with said first reference.

14. The computer system of claim 13, further comprising means for storing said modified group of related data records to a data storage device.

15. The computer system of claim 12, wherein said means for parsing related data records comprises searching for a hypertext link.

16. The computer system of claim 15, wherein said first address is created from information determined by parsing data selected from the group consisting of said first reference and a data record from said related group of data records.

17. The computer system of claim 16, wherein said computer system is a hospital medical system and said first reference comprises patient identification information.

18. The computer system of claim 12, wherein said means for parsing related data records comprises searching for a keyword phrase.

19. The computer system of claim 18, wherein said first address is created from information determined by parsing data selected from the group consisting of said first reference and a data record from said related group of data records.

20. The computer system of claim 19, wherein said group of related data records are converted from a format not supported by said display program to one that is supported by said display program.

21. The computer system of claim 20, wherein said computer system is a hospital medical system and said first reference comprises patient identification information.

22. The computer system of claim 14, wherein each of said group of related data records are stored at addresses created using information determined by parsing data selected from the group consisting of said first reference and a data record from said related group of data records.

23. The computer system of claim 22, wherein said second data record is stored at a fourth address created by using information determined by parsing at least one of said first address and said second record.

24. A method of collecting a group of related data records on a computer system and storing said data records in a manner permitting their retrieval in an ordered manner and display by an interactive display program capable of displaying a plurality of interface supported data formats, comprising:

(a) receiving a first reference to a group of related data records from an accessory computer system;

(b) retrieving said group of related data records using information in said first reference, a list of databases and a list of instructions for retrieving each data record;

(c) creating a reference to each of said related data records;

(d) creating a master control file and a plurality of secondary control files;

(e) determining in which of said master control and said secondary control files said reference is to be placed by using information in a list of data types;

(f) storing said group of related data records and said master control file and said secondary control files to a data storage device.

25. The method of claim 24, wherein associated software required to present said group of related data records is retrieved and stored on said storage device.

26. The method of claim 24, further comprising the step of parsing each of said group of related data records to locate a second reference to a first data record.

27. The method of claim 26, further comprising the step of retrieving and storing said first data record on said data storage device.

28. The method of claim 26, wherein the step of parsing for a second reference includes searching for a hypertext link.

29. The method of claim 28, further comprising the step of modifying said second reference to create a first address from information determined by parsing data selected from the group consisting of said first reference and a data record from said related group of data records.

30. The method of claim 29, further comprising the step of converting said group of related data records and said second data records from a format not supported by said display program to one that is supported by said display program.

31. The method of claim 30, wherein the computer system is a hospital medical system and said first reference includes patient identification information.

32. The method of claim 26, wherein the step of parsing for a second reference includes searching for a keyword phrase.

33. The method of claim 32, further comprising the step of modifying said second reference to create a first address from information determined by parsing data selected from the group consisting of said first reference and a data record from said related group of data records.

34. The method of claim 33, further comprising the step of converting said group of related data records and said second data records from a format not supported by said display program to one that is supported by said display program.

35. The method of claim 34, wherein the computer system is a hospital medical system and said first reference includes patient identification information.

36. The method of claim 24, wherein each of said group of related data records are stored at addresses created using information determined by parsing data selected from the group consisting of said first reference and a data record from said related group of data records.

37. The method of claim 24, wherein the data type of each said related data record as used to determine the placement of said reference in said master control, secondary control, or tertiary control files.

38. The method of claim 37, wherein date and time of each said related data record is used to determine the placement of said reference in said master control, secondary control, or tertiary control files.

39. A computer system for converting a plurality of data references within a plurality of data records on a plurality of databases into hypertext links using standardized addresses, said computer system having a user interface with an interactive display program for displaying a plurality of interface supported data formats, and comprising:

(a) a list of said databases;

(b) means for retrieving all data records within each of said databases, wherein each of said data records is stored in a file referred to by a file name;

(c) means for creating storage addresses for each of said data records based upon information determined by parsing data selected from the group consisting of said file name corresponding to said data record and the contents of said data record;

(d) means for parsing each of said data records to identify a reference to a data type;

(e) means for modifying each occurrence of said reference to create a specific address for each said data record, wherein each said specific address is operable to retrieve the corresponding data record of said data type related to each of said data record;

(f) means for storing each of said modified data records to a data storage device at said plurality of storage addresses.

40. The computer system of claim 39, wherein the means of parsing for a second reference comprises searching for a hypertext link.

41. The computer system of claim 40, wherein said first address is created from information determined by parsing data selected from the group consisting of said file name and the contents of each corresponding said data record.

42. The computer system of claim 41, wherein the computer system is a hospital medical system.

43. The computer system of claim 41, where each of said data records are converted from a format not supported by said display program to one that is supported by said display program.

44. The computer system of claim 39, wherein the means of parsing for a second reference comprises searching for a keyword phrase.

45. The computer system of claim 44, wherein said first address is created from information determined by parsing data selected from the group consisting of said file name and the contents of each corresponding said data record.

46. The computer system of claim 45, wherein each of said data records are converted from a format not supported by said display program to one that is supported by said display program.

47. The computer system of claim 46, wherein the computer system is a hospital medical system.

* * * * *